United States Patent [19]

Moriarty et al.

[11] Patent Number: 4,992,380
[45] Date of Patent: Feb. 12, 1991

[54] CONTINUOUS ON-STREAM MONITORING OF COOLING TOWER WATER

[75] Inventors: Barbara E. Moriarty, Naperville; James J. Hickey, Palos Heights; Wayne H. Hoy, Burbank; John E. Hoots, St. Charles; Donald A. Johnson, Batavia, all of Ill.

[73] Assignee: Nalco Chemical Company, Naperville, Ill.

[21] Appl. No.: 258,131

[22] Filed: Oct. 14, 1988

[51] Int. Cl.$^5$ .............................. G01N 35/08
[52] U.S. Cl. ...................... 436/55; 422/62; 422/82.02; 436/147; 436/150; 436/164
[58] Field of Search .................. 422/62, 82.02; 436/38, 436/55, 150, 164

[56] References Cited

U.S. PATENT DOCUMENTS

| | | |
|---|---|---|
| 3,561,935 | 2/1971 | Beal .................................. 422/62 X |
| 4,023,022 | 5/1977 | Mukae et al. ...................... 422/62 X |
| 4,648,043 | 3/1987 | O'Leary . |
| 4,783,314 | 11/1988 | Hooks et al. ...................... 422/62 X |

Primary Examiner—Charles Hart
Attorney, Agent, or Firm—Kinzer, Plyer, Dorn, McEachran & Jambor

[57] ABSTRACT

The performance of a treating agent added to a body of water employed in a cooling tower is continuously monitored by real-time analysis of a spectral or chemical characteristic of an inert tracer proportioned to the treating agent, said characteristic being indicative of tracer concentration, and converted to a voltage analog. The voltage analog is compared to a monitor value representing par performance and if performance is nonstandard (nonpar) a signal is generated which alters the output of a pump which feeds the dosage of treating agent containing proportioned tracer.

20 Claims, 11 Drawing Sheets

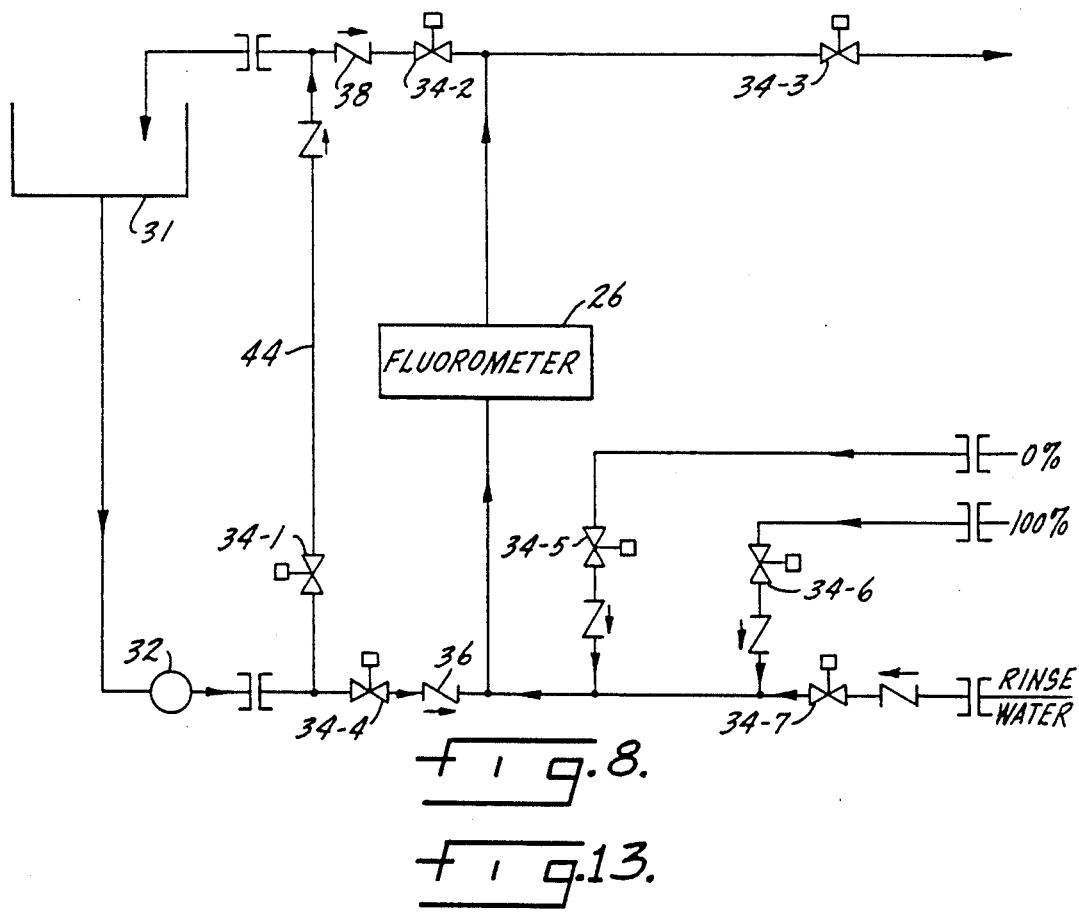
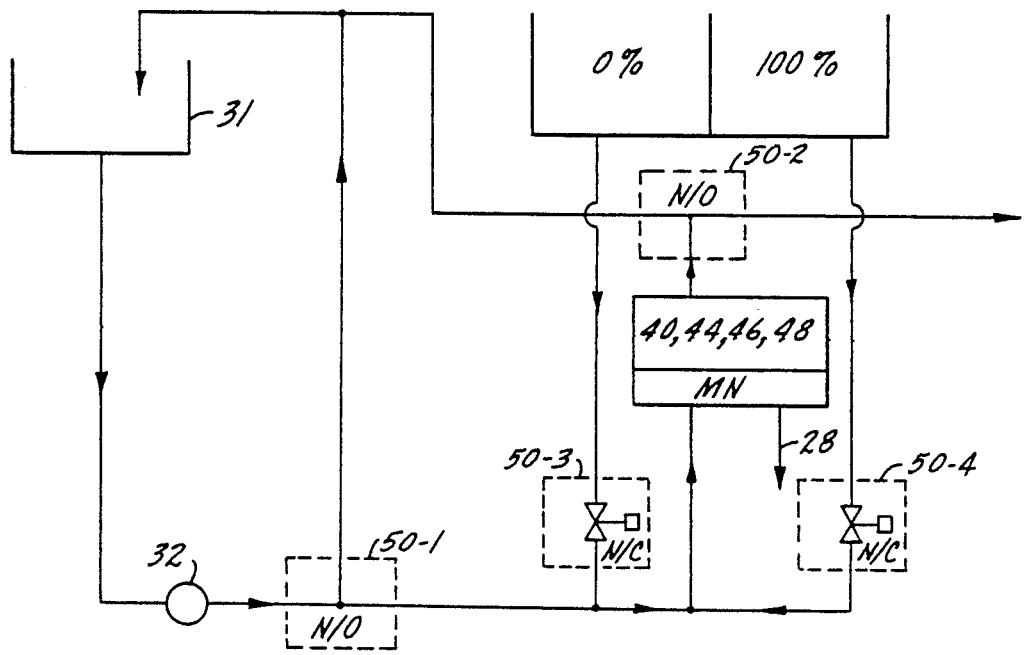
Fig. 8.
Fig. 13.

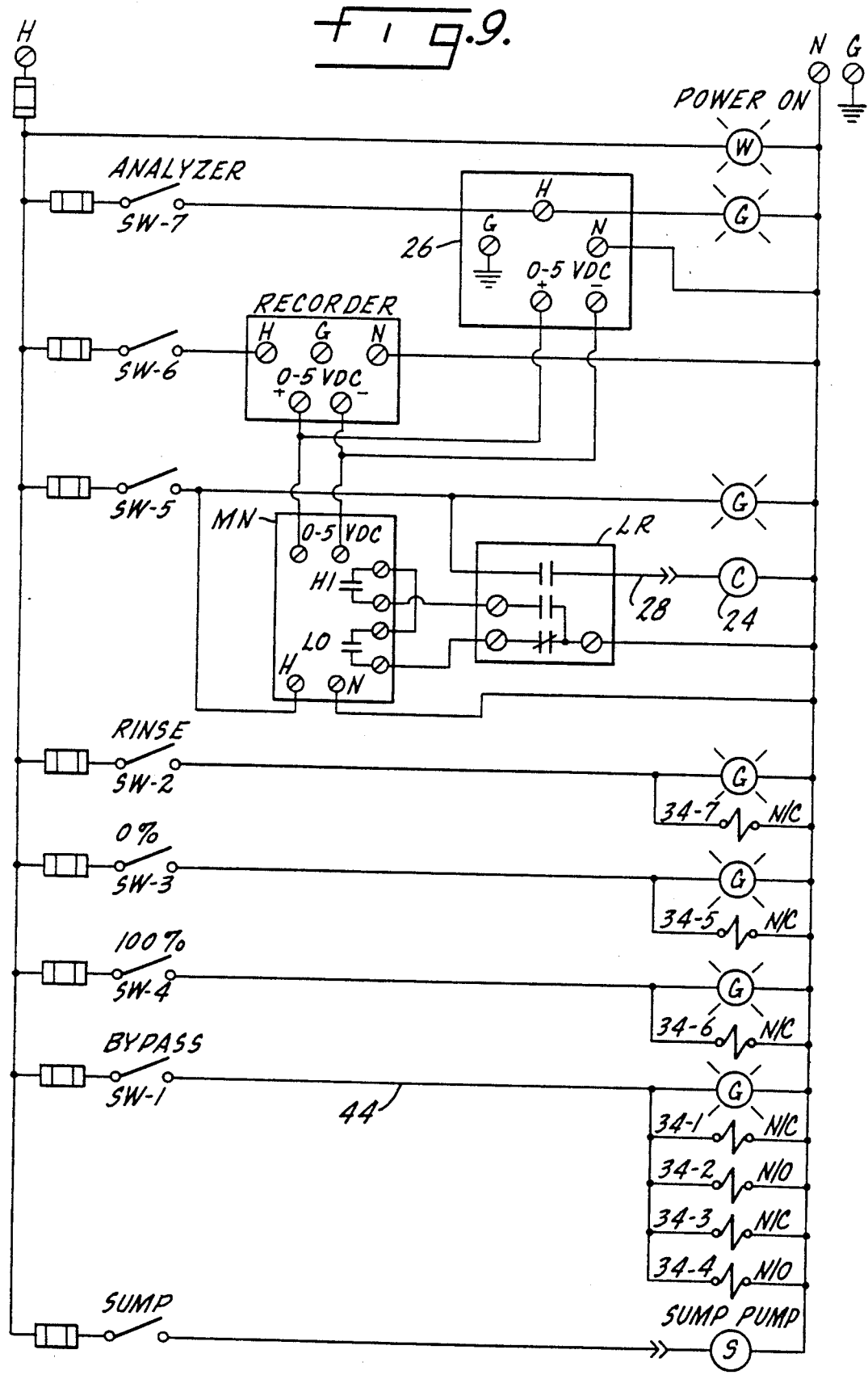

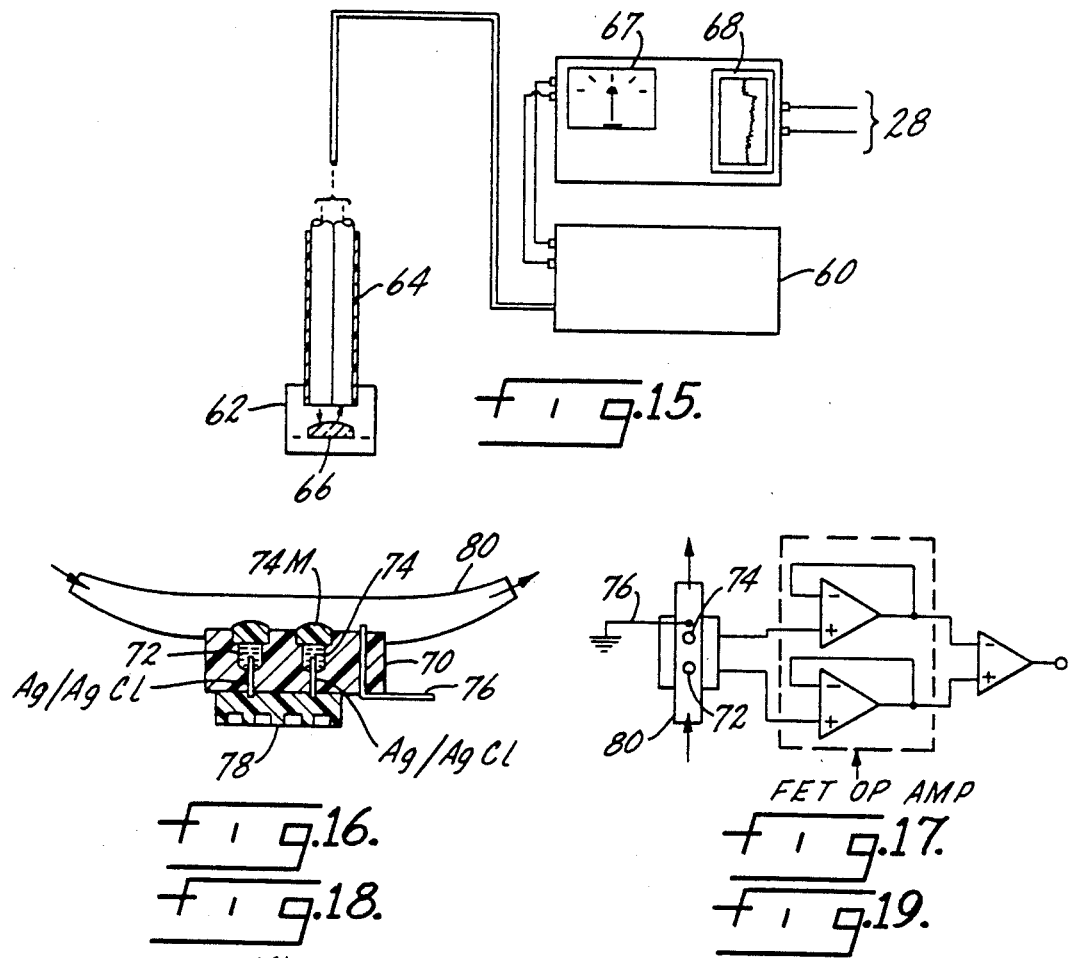

CONTINUOUS ON-STREAM MONITORING OF COOLING TOWER WATER

FIELD OF THE INVENTION

This invention relates to systems for continuous on-stream monitoring of the performance of a treating agent added to a circulating body of water, and especially a circulating body of water in a cooling tower which may have unknown sources of water gains or losses effecting the concentration of the treating agent.

BACKGROUND OF THE INVENTION: GENERAL

Aqueous industrial cooling systems that employ cooling towers usually require chemical treating agents to prevent corrosion, scaling and other encroachments which lessen efficiency.

Historically chemical treatment has normally consisted of acid and various heavy metals which were easy to test for. These compounds also had broad application ranges over which they were effective. This made the treatment process relatively painless.

Now, circa 1988, chemical treatment of industrial cooling water is far more complex. As environmental concern has heightened, heavy metals have given way to organics, acrylamides, acrylates, organic phosphates and triazoles, etc. Unfortunately, all these new treatment programs are quite difficult to test for. Exacerbating the situation is the additional fact that virtually every one of them requires very tight control to perform in an optimum manner Various approaches have been tried to resolve this dilemma. Efforts to simplify tests, ratio chemical feed to either system make-up or blowdown, etc., have all been examined and, by and large, found wanting Almost all attempts to automate the precise addition of chemicals to cooling towers have been defeated by the unknown variables and unknown volumetric water changes inherent in these systems. Evaporation rates vary with changes in ambient wet bulb temperature; and cooling towers lose unknown amounts of water due to windage, drift, overflow, leaks, and uses of system water besides cooling. Also, it is common practice in many large plants to dispose of various extraneous water streams (process condensates, tramp bleeds, etc.) by returning them to the cooling tower on an unregulated basis. All these variables become unknown water gains and losses.

On the basis of these experiences, and the inability of industry to develop accurate, dependable tests for the types of treatment compounds in use, advanced technology is needed to determine the performance of the treating agent.

Research projects of considerable magnitude have been funded to find materials that can be employed as easily measurable indicies of the amount of product (treating agent) present in the system. One such project is disclosed in application Ser. No. 019,454, filed Feb. 26, 1987 now U.S. Pat. No. 4,783,314.

While the present invention addresses a system (instrumentation) for continuous monitoring, as expressed above, a background of complex chemistry is also involved because the instrumentation analyzes the concentration of a tracer (parts per million tracer=ppm T) added proportionally with the treating agent (ppm A).

The tracer must be transportable in the waste system without change In actual use, the treating agent will be consumed If actual performance of the treating agent conforms to the theoretical performance (postulated rate of consumption) the ratio of tracer to treating agent will increase.

Thus, the tracer, to serve as an index of the product or treating agent performance must fulfill several criteria.

Firstly, selected chemicals must be detectable on a continuous or semicontinuous basis. Measurements of concentration must be accurate, repeatable and capable of being performed on many different waters (i.e. clean, turbid, hard, soft, etc.).

Secondly, the tracer material cannot be one already present in a significant quantity in the water used for industrial cooling.

Thirdly, testing for the tracer cannot be interfered with, or biased, by other chemical compounds normally present in cooling water.

Fourthly, the tracer must not reduce the efficacy of such active ingredients of the treatment chemicals themselves as poly acrylic acid, poly (acrylate/acrylamide) copolymers, acrylate/acrylamide/amino methane sulfonic acid, acrylate/methacrylic acid/t-butylacrylamide, 1-hydroxyethane-1, 1-diphosphonic acid, 2-phosphonobutane-1,2,4- tricarboxylic acid, sodium tolytriazole, etc.

Fifthly, since the tracer must be added with the treating agent, the material selected as the tracer must be compatible with the actives (treating agents) such as those enumerated above with respect to formulation, storage, freeze-thaw recovery, etc.

Lastly, the tracer cannot be toxic, or represent any sort of environ metal problem upon discharge. Ideally, any material used in the tracer role would be completely biodegradable.

The enormity of the chemistry complex of on-site water employed in a cooling tower can be appreciated from a mathematical composite of over 500 typical on-site samples subjected to laboratory analysis under our auspices Table I presents the average:

TABLE I

| Parameter | Concentration |
|---|---|
| Ca | 650 ppm |
| Mg | 200 ppm |
| NaCl | 200 ppm |
| $SO_4$ | 30 ppm |
| pH | 8.5 ppm |
| $HCO_3$ | 300 ppm |
| $CO_3$ | 20 ppm |
| Fe | 1.0 ppm |
| Mn | 0.1 ppm |
| $Cl_2$ | 0.25 ppm |
| $NH_3$ | 3 ppm |
| Zn | 1.0 ppm |
| SS* | 20 mg/l |
| $PO_4$ | 10 ppm |
| Na | 150 ppm |
| Molybdate | 10 ppm |
| K | 2 ppm |

*suspended solids

OBJECTS OF THE INVENTION

From such considerations, the primary object of the present invention is to develop a system for continuous on-stream monitoring of a water soluble tracer employed quantitatively with a treating agent incorporated in a circulating body of water, the system including a flow cell and a comparator (evaluating means) by which a voltage equivalent of the concentration of tracer in the flow cell can be compared to that of a standard in the comparator representing par performance of the treating agent; any difference in voltage, deemed nonstandard, will result in a voltage output (signal) which controls a pump to feed more or less treating agent and proportioned tracer, until the output voltage of the flow cell detector is restored to par.

Other objects of the invention are to be able to diagnose the water system continuously on a real-time basis, to be able to distinguish momentary anomalies from real errors and to be able to quantify the time required to restore the system to steady-state treating agent performance.

Another object is to incorporate in the system means by which the instrumentation can be calibrated from time to time after prolonged use on a continuous basis; specifically to first isolate the flow cell, then to rinse it, then to calibrate it, and then to reinsert the instrument for on-stream continuous monitoring.

BRIEF DESCRIPTION OF THE DRAWING

FIGS. 3A–C are diagrams showing the operation of a water treatment program containing a tracer as a function of time;

FIG. 8 is an on-stream diagram of the present instrumentation;

FIG. 9 is a wiring diagram of the FIG. 8 instrument;

FIG. 13 is a water flow diagram of an alternate monitoring continuous feedback control instrument;

FIGS. 14-1, 14-2, 14-3 present a wiring diagram of the instrument represented in FIG. 13;

FIG. 15 is a schematic view of the invention when using a colorimeter;

FIG. 16 is a detail sectional view showing how an ion selective electrode may be employed in practicing the invention;

FIG. 17 is a schematic view of the electrode of FIG. 16 coupled to a transistor; and FIGS. 18 and 19 are graphs of the distribution of treatment concentration values.

INTRODUCTION TO THE PERFORMANCE OF AN INERT TRACER

Figure 1:
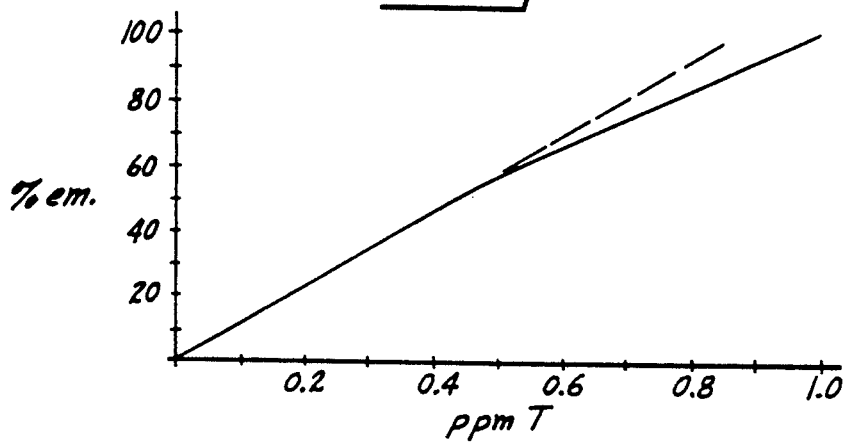
FIG. 1 presents curves showing the performance of a fluorescent tracer (T) in terms of emissivity vs. concentration, the solid line representing observed values and the dashed line is theoretical behavior.

In a system involving a body of liquid to which a treating agent is added, maintaining the proper feed rate and concentration for the agent is essential for optimal performance, especially in a cooling tower or circulating water system where the cooling water is being circulated either on a once-through basis or constantly recirculating. Improper feed rate and concentration of treating agent can lead to serious problems. For example, severe corrosion and/or deposit formation can rapidly occur on heat-exchange surfaces in cooling and boiler water systems when an incorrect concentration of treating agent is used. One way of estimating the concentration of a treating agent is to measure the level of an active component in the treatment formulation (e.g. polymeric scale inhibitor, phosphate, or organophosphonate). That technique is often unsatisfactory due to one or more of the following problems:

background interferences from the system liquid or materials contained in the liquid;

analytical methods use bulky and costly equipment;

time-consuming, labor-intensive analyses are not compatible with continuous monitoring;

inaccurate readings result from degradation or deposition of active component within the system.

An alternative method of determining treatment feed rates is to specifically add metal ions (e.g. $Li^+$) to the formulation or system. That method helps circumvent the degradation/deposition and background interference problems. However, quantitation of low tracer levels commonly magnifies problems associated with expensive equipment and time-consuming test methods. Additional factors which must be considered are cost and environmental acceptability of the tracer. For example, radioactive tracers are detectable at very low levels, but are generally expensive and unacceptable due to environmental and health concerns.

In general, and in comparison, the concentration of an inert water soluble tracer such as a fluorescent tracer may be directly determined from a calibration curve of tracer concentration versus instrument response, permitting (see FIG. 1) the determination of the concentration range from parts per million (ppm) to part per trillion (ppt).

In addition, multiple tracers may be used concurrently by choice of tracers with proper spectral or ion activity characteristics. As such, various combinations of tracers, for example, and treatment feeds can be quantified within a liquid system. For example, four individual treatments containing a single unique tracer plus one additional treatment containing the two tracers could be employed within a liquid system. In that case, each tracer and the corresponding individual concentration of the five treatments can each be quantified. In addition to being able to quantify complex combinations of the treatment feeds, environmentally acceptable water soluble compounds are available which are not degraded by or deposited within the liquid systems, and are available at low cost. This is termed an inert tracer herein, inert to the system equipment and all chemistry in the system, so the tracer moves through the system unscathed and not altered to any significant or meaningful extent. All tracers identified herein subscribe to the practical analytical chemistry requirement of loss equal to or less than 10%. All of this makes possible (a) direct addition of from one or more tracers to a liquid system;

(b) incorporation of one to six (or even more) tracers into a chemical treatment composition containing other components, said treatment being applied to the liquid system in order to maintain proper operation of that system;

(c) addition of one to six chemical treatment agents (or even more) containing tracer(s) directly into liquid system or into liquid feed leading into system;

(d) addition of tracers so that within the liquid system individual tracer concentrations ranging from 1 part per trillion to 100 parts per million (ppm), preferably from 1 part per billion (ppb) to 10 ppm, and most preferably from 10 ppb to 2 ppm are realized.

Figure 2:
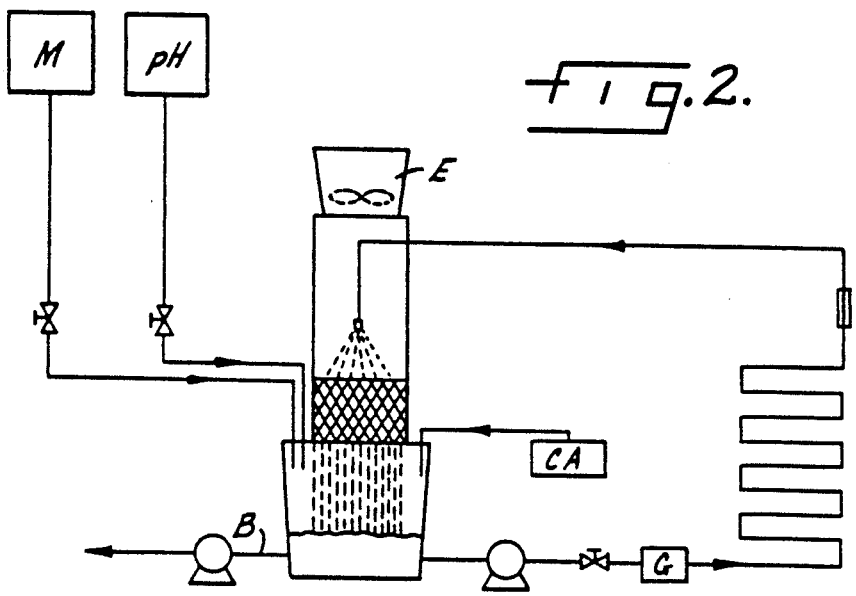
FIG. 2 is a diagram of a water cooling tower system.

In all cooling tower systems, when operable and on-stream continuously, energy is extracted by the recirculating cooling water from the process side of the system which is at a higher temperature. This is shown in FIG. 2. To maintain the efficiency of that heat transfer, energy is removed by evaporative cooling of the recirculating water in the cooling tower and the heat-exchanger surfaces need to remain clean. Evaporation (E) of the cooling water leads to concentration of the suspended and dissolved solids in the cooling system. The term concentration ratio (CR) is a measure of the increased level of dissolved and suspended matter in a system (eq 1).

$$CR = \frac{\text{concentration of salts in cooling water}}{\text{concentration of salts in makeup water}} \quad \text{(eq 1)}$$

Deposition of solids and corrosion of heat-exchanger surfaces are the problems most generally encountered. Cooling water systems commonly contain highly supersaturated levels of scaling salts Deposition of solids throughout the system (particularly at metal heat-exchangers) will occur unless chemical treatment(s) containing scale inhibitors is added. To prevent corrosion of metal heat-exchangers and water transfer lines, chemical treatment(s) commonly contains corrosion inhibitors. If the feed rate of the chemical treatment is too high or too low, severe scaling and corrosion can occur on the heat-exchangers and throughout the system.

It is vital that the level of dissolved and suspended solids, total volume of the system liquid ($V_T$) and concentration of chemical treatment be maintained between certain values in order to provide economical usage of water, efficient heat transfer, minimal fouling of entire cooling systems, and low operating costs. To maintain the concentration ratio (CR) within an acceptable range, water containing a "high" concentration of impurities must be removed from the system [collectively defined as "blowdown" (B)] and replaced by water containing a "low" concentration of impurities [collectively defined as "makeup" (M)]. The values for E, B, M, and CR are variable due to changes in the weather, operating conditions of the industrial plant, and quality of the makeup water. Those factors are all interrelated (as shown below) and a change in any one of those factors must be counterbalanced by corresponding changes in other operating parameters.

$$B + M = E \quad \text{(eq 2)}$$

$$CR = M/B \quad \text{(eq 3)}$$

In addition to the dynamic operating conditions of a cooling water system, other significant variables and unknown factors are commonly encountered. For example, blowdown water (B) can be removed from the cooling system through a variety of ways (eq 4), which in actual practice tend to be variable and ill-defined in nature; indeed a major problem is there can be unknown or unquantified sources of water gain, as well as loss, in very large volumes. The rate at which water is specifically pumped from the cooling water system is defined as "recirculating water blowdown" ($B_R$), and even that rate is not always accurately known due to practical difficulties in measuring large volumes of water. In addition, ill-defined amounts of recirculating water (unaccounted system losses) are commonly removed from the cooling water system to be used in other areas of the industrial plant, defined as "plant blowdown" ($B_p$). Water may be tapped off in large amounts for many different purposes and at different times, not known to the supervisor responsible for administering the correct dosage of treating agent. In one instance, as another example, it was not known that large volumes of blowdown water from one cooling tower were being fed to another cooling tower. These are good examples of why it may be meaningless to adjust the treating agent dosage on the basis of monitoring a system parameter such as makeup or blowdown volumes.

Leakage of recirculating water ($B_L$) and drift (misting) of liquid droplets from cooling tower ($B_D$) also add to unaccounted system losses. A similar situation can occur with the makeup water, where the total makeup water rate (M) is the combined rate at which makeup water is specifically pumped into the recirculating system ($M_R$) and liquid originating from other sources (M'). The complexity of the situation can be appreciated by considering equations 2-5.

$$B = B_R + B_p + B_L + B_D \quad \text{(eq 4)}$$

$$M = M_R + M' \quad \text{(eq 5)}$$

The feed rate of chemical treatment into the cooling water system is commonly based on estimated values for $M_R$ or $B_R$, which means there can be considerable uncertainty regarding the concentration of the chemical treatment. When operating conditions of the cooling water system change, the feed rate of the chemical treatment should be adjusted. Those adjustments may or may not be made, depending on how carefully the cooling water system is monitored and controlled. Even when feed rates are adjusted, the concentration of chemical treatment within a cooling water system ($V_T$) generally may respond slowly to the change (eq 6).

$$t = (V_T/B)\ln\left[\frac{1}{(1-x)}\right] \quad \text{(eq 6)}$$

where t = response time for a change to occur and
x = % change of concentration (decimal)

For example, consider a representative system containing one million gallons and total blowdown rate of 300 ga/min. If the treatment feed rate is increased from 50 to 100 ppm, 38.5 hours are required for only half of that change (25 ppm increase in treatment concentration) to be attained, assuming that no other fluctuations or changes have occurred within the system. For very large values of $V_T$ and small values of B, response time may be measured in days or weeks. In other cases, changes can occur rapidly, such as purposeful (or inadvertent) flushing of the system. Therefore, it is important that good control and accurate monitoring of the system be maintained.

Another significant operating parameter which should be quantified is the holding time index (HTI), a measurement of the half-life (50% change) of a chemical species within the system (eq 7).

$$HTI = 0.693 \, (V_T/B) \qquad (\text{eq 7})$$

Under severe operating conditions, it is important to optimize HTI in order to reduce possible degradation of components in the chemical treatment without greatly increasing operating costs.

Due to all the operating limitations and uncertainties in cooling water systems, the need to rapidly determine and continuously monitor the concentration of chemical treatments is clearcut. The addition of an inert tracer to the chemical treatment permits accurate determination of all the unknown, imprecisely known and variable operating conditions previously described.

FIGS. 3A-C demonstrate the operation of a water treatment program at the molecular level as a function of time. The concentrated chemical treatment (which contains one or more components) is slowly fed into the recirculating cooling water where the treatment is rapidly diluted and distributed throughout the system. If operating conditions of the cooling water system remained constant, the addition and removal of treatment (due to recirculating water blowdown and system losses) would equilibrate (FIG. 3A). The concentration of the chemical treatment and its components ideally should remain unchanged. However, that situation never occurs. As time progresses (FIGS. 3B-C), additional amounts of zinc and phosphorus-containing compounds can be lost from the recirculating water due to deposition and protective-film formation on metal surfaces and chemical/biological degradation processes. Also, changes in operating conditions (blowdown rate, concentration ratio, and product feed rate, and others) affect concentration of treatment components. Without an inert tracer, analysis of the recirculating water may measure current concentrations of some of the treatment components but cannot directly indicate the original feed rate of the treatment. Use of an inert tracer to quantify the treatment feed rate and concentration is a valuable addition to current water treatment programs.

FIGS. 3A-C also indicate how addition of an inert tracer provides accurate determination of treatment efficacy and feed rate in spite of deposition of other components in the chemical treatment. For example, assume the treating agent (also termed "product" or "treatment") feed rate was 100 ppm. If deposition occurred on the heat-exchangers so that 40% of the phosphorus-containing species could be lost from the recirculating water, but the tracer would not be lost in the practical analytical sense defined above. The total phosphorus concentration would suggest only 60 ppm of treatment was present. The tracer would indicate that 100 ppm of treatment was added and a loss of phosphorus-containing components equivalent to that supplied by 40 ppm feed of treating agent was being deposited. Determination of loss rates of active component(s) of the treatment is a direct measurement of treatment efficacy.

In summary, important system characteristics of many industrial systems (total volume, blowdown and makeup rates, holding time index, treatment feed rates and others) are imprecisely known, variable and sometimes unpredictable in nature. Lack of knowledge regarding those factors can lead to serious deposit and corrosion problems throughout the entire cooling water system. In particular, over/underfeeding of treatment program or improper operation of cooling water system can result in significant loss of treatment component(s) and adversely affect heat transfer within a cooling water system. In addition, water treatment programs commonly contain regulated or toxic materials (e.g. zinc ions, phosphate, or chromate). Overfeeding of treatments can be hazardous and makes it more difficult for industrial sites to meet government restrictions on water effluent and atmospheric discharges. Use of an inert tracer is a highly desirable means of accurately determining, continuously monitoring, and controlling cooling water system characteristics and treatment feed rates and concentration within desirable ranges.

The successful use of inert tracers to accomplish the tasks described above has been accomplished. Pilot cooling tower tests have clearly demonstrated the concept and feasibility of using tracers in treatment formulations and field testing has proven applicability of tracers in real world systems.

Tests were conducted in pilot cooling towers (FIG. 2) designed to simulate an industrial cooling water system. Processes such as recirculating water, chemical treatment feed, deposit formation and corrosion on heat-exchangers, blowdown and makeup, and evaporative cooling from tower fill are all included. A significant feature of this laboratory system is that tracer determination of system volume and treatment feed rates can be corroborated by alternative direct measurements.

Figure 4:
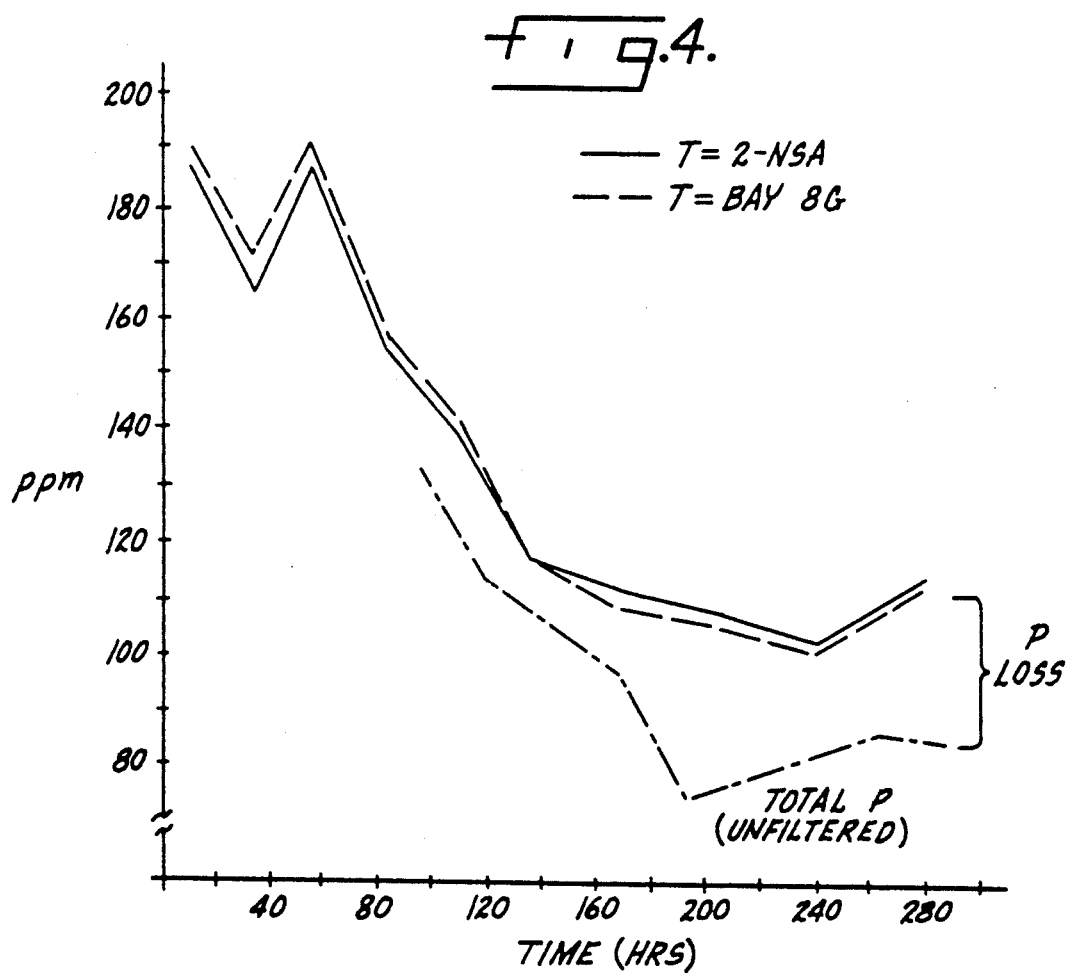
FIG. 4 presents curves of two fluorescent tracers used in a water system treatment program.

Results from a PCT test are summarized in FIG. 4. A single water treatment formulation was used and contained two fluorescent tracers [sodium salt of 2-naphthalenesulfonic acid (2-NSA) and Acid Yellow 7 dye, (BAY8G] a polymer (scale inhibitor), organophosphorus compounds (scale and corrosion inhibitors), and aryltriazole (corrosion inhibitor for brass). Each fluorescent tracer was quantified individually by choosing widely separated wavelengths of light to excite the individual tracer and by observing fluorescent emission at widely separated wavelengths of light for each tracer, according to the method diagrammed in FIG. 5. A dilute solution (100 ppm) of treatment was used as a reference standard and all concentrations of tracers and phosphorus-containing species (total phosphorus content) are expressed as an equivalent formulation concentration.

Figure 5:
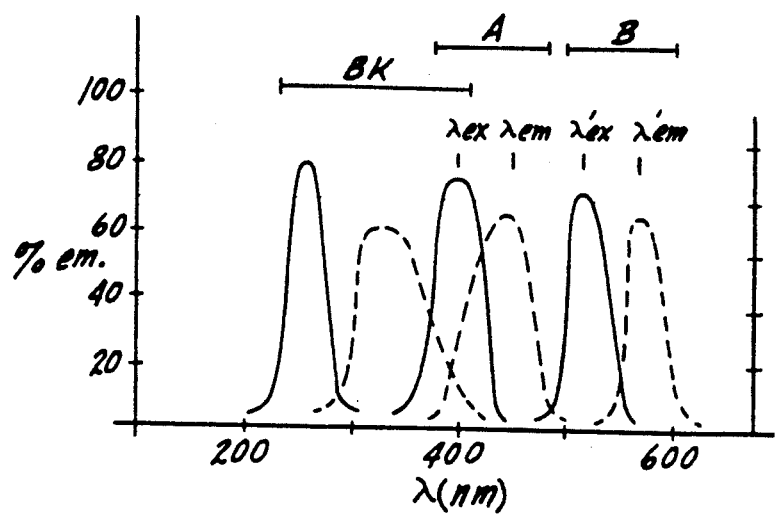
FIG. 5 presents curves showing the concept of selectively measuring two fluorescent tracers (A and B) in the presence of a fluorescent background (BK) where the horizontal axis is the wavelength of light in nanometers (nm)

The aryltriazole corrosion inhibitor in the formulation described above is fluorescent. However, proper choice of the wavelengths of light for excitation and observation of fluorescent emission of the 2-NSA and BAY8G tracers circumvented potential interference by the aryltriazole. The underlying principles regarding quantitation of individual fluorescent tracers and avoiding interference from other fluorescent compounds are shown in FIG. 5.

The PCT system was initially dosed with 192 ppm of formulation based on a total system volume of 52 liters. Initial tracer readings of Acid Yellow 7 and 2-NSA indicated 190 ppm and 186 ppm of treatment were slugged into the PCT system, which would respectively correspond to system volume values of 52.5 and 53.1 liters. The tracer results were internally consistent and provided an accurate measure of the system volume.

During the PCT's first 40 hours of operation, the blowdown pump was off and the recirculating water was being concentrated by evaporation from a concentration ratio of one (makeup water) up to a value of four (refer to eq. 1). During that time, drift from the cooling tower is the only loss of recirculating water from the system and should cause a small and equal decline in the level of each fluorescent tracer. That response is precisely what was observed. Between 40–48 hours, the blowdown of recirculating water was used to maintain a constant concentration ratio and the treatment was fed into system at a rate of 213 ppm whenever blowdown occurred. As such, a small and equal increase in the concentration of each fluorescent tracer should be observed during that time period, which was the case. Between 48 hours and completion of the test, treatment was fed at an average rate of 112 ppm whenever blowdown of the system occurred. During that time, the level of each tracer should undergo an equal and exponential decrease (refer to equation 6) and finally level off at a concentration approaching 112 ppm after about 190 hours. From 190 hours until the end of the test, the concentration of each tracer may undergo relatively small and equal increases or decreases in response to variations in the PCT operating conditions (e.g. changes in blowdown rate, concentration ratio, etc.). That predicted behavior for each fluorescent tracer was exactly what was observed throughout the entire PCT test (FIG. 4).

Comparison of the treatment feed rate in the recirculating water predicted by the fluorescent tracer levels versus total phosphorus concentration demonstrates the superior accuracy of these tracers and their ability to determine treatment efficacy. After 190 hours the total phosphorus level indicated a treatment concentration of 75–86 ppm, whereas the tracer indicated the treatment level was averaging 110 ppm. The differences in those levels arise from deposition of the organophosphorus components of the treatment onto the heat-exchanger tubes. The difference(s) between the tracer level(s) and the total phosphorus level is a direct measure of treatment effectiveness, since it quantifies how much of the active phosphorus-containing components are being lost within the system from deposition, degradation and corrosion processes. In an operating system with no loss of active treatment components, the total phosphorus and tracer levels would all indicate nearly identical treatment concentration.

Upon completion of the PCT test, the solid deposits from the heat-exchange tube were removed and analyzed. A high rate of deposit formation was measured (54 mg/day), whereas 35 mg/day was considered to be the maximum acceptable limit. The total phosphorus content of the deposit was 10.4 wt % (as orthophosphate) and is consistent with deposition of the organophosphorus-containing treatment components, as previously described. In spite of the high scaling rate no detectable amount (<0.003 wt %) of either BAY8G or 2-NSA was observed, which verifies the inert and non-absorbing nature of those fluorescent tracers.

An industrial system, field tested, was being operated under severe conditions as follows total system volume was imprecisely known and blowdown rate was incorrectly measured;
long holding-time index and large volume of recirculating water;
high skin temperatures on heat-exchange tubes;
low flow of cooling water experienced in some areas;
moderate level of particulate matter present;
significant variations in concentration ratio;
system had not been pretreated to minimize possibility for adsorption of tracer on surfaces and deposits;
high average flow rate of recirculating water (~100 million gallons/day).

The system investigated was a complicated (but typical) recirculating water system including a cooling tower used to cool high-temperature process-side fluids. However, that cooling tower and system could just as well have been one used with any industrial process in which the energy is extracted by heat-exchange with a moving body of water, whether once-through or recirculating. There were numerous points for bleedoff or blowdown of recirculating water, and likewise several sources of makeup water was possible.

Initially, a treatment program comprised of a fixed ratio of corrosion inhibitors ($Zn^{+2}$ and inorganic/organic phosphorus compounds), a polymeric scale inhibitor (to prevent deposition of scaling salts and corrosion inhibitors within the system) was fed into the cooling water system. The first treatment did not contain a fluorescent tracer and the rate of treatment feed was based upon a flowmeter reading from the blowdown pump. Analysis of the recirculating water revealed unexpectedly low levels of zinc, phosphorus, and polymer. At that point, it was not known whether the low treatment levels were due to deposition/degradation of the treatment components, poor analytical results, or a low feed rate of treatment. It became essential to quantify the system's operating characteristics and determine if the chemical treatment was functioning properly.

Figure 6:
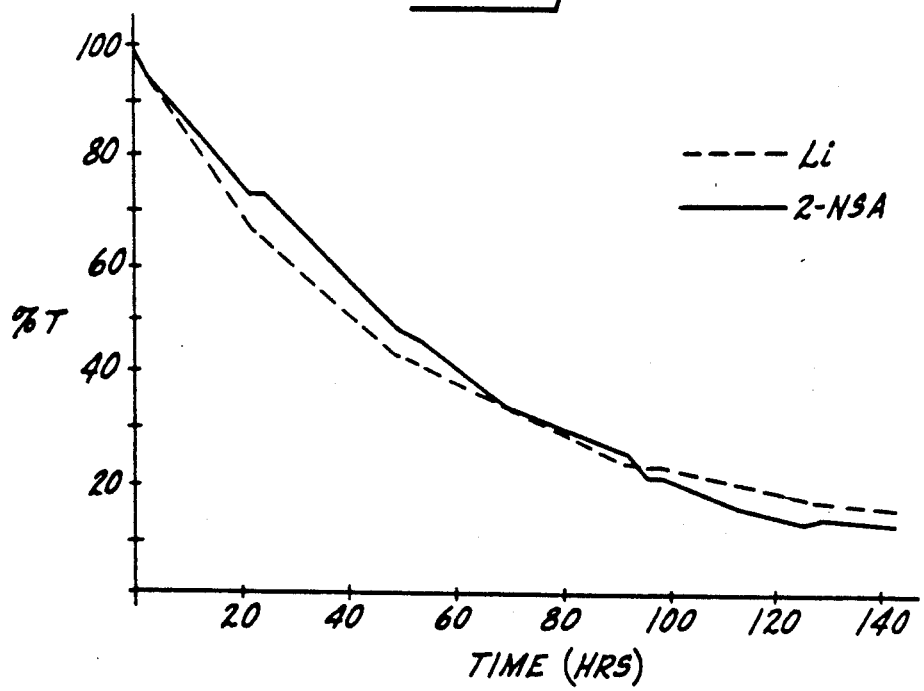
FIG. 6 presents curves showing lithium (grab sample) used to test accuracy of a fluorescent tracer.

To determine the reason(s) for the low levels of chemical treatment components being observed, an inert fluorescent tracer, a sodium salt of 2-naphthalenesulfonic acid (2-NSA) was employed in the following tests:

Test A - "slug-feed and die-away" study using dual tracer combination with known amounts of lithium chloride and fluorescent 2-NSA added to the system (refer to FIG. 6).

Test B - a known amount of 2-NSA was added to the treatment formulation (which was slowly fed into the system) as previously described in example 1.

The 2-NSA fluorescent tracer is inert to the cooling water system in the sense of not being reactive with any other components in the body of water and incapable of coupling or depositing in any manner with the system equipment under the accepted analytical limits mentioned above. Because the fluorescent tracer is thus capable of remaining as a discrete and unchanged entity which permeates throughout the circulating system, the tracer is a true indicator of treatment feed rate and characteristics of the cooling water system.

The "slug-feed and die-away" studies (Test A, FIG. 6) are classical procedures for determining total removal of recirculating water from system (blowdown+system leakage+unaccounted system losses+cooling tower drift) and total volume of cooling water system. By adding a known amount of the tracer and measuring its concentration after it has permeated the system, the total system volume can be quantitatively measured. Li+ has been previously used as an inert, nonabsorbing tracer in "slug-feed and die-away" studies. However, lithium is very expensive to use, cannot be monitored continuously and quantitative analysis requires atomic adsorption or emission spectrophotometric equipment, and a significant pre-existing background of lithium is present in some systems'. The 2-NSA fluorescent tracer provided comparable results to Li+, but a much smaller amount (one-sixth the mass and 1/30th the cost) of 2-NSA was required as compared to Li+. In addition, quantitative analysis of 2-NSA in a cooling water system (by comparison of fluorescence emission to a reference solution of 2-NSA) is much simpler and more rapid than AA (atomic absorption) analysis of lithium. Furthermore, a significant pre-existing background of 2-NSA has not been encountered in industrial application sites. The slug feed of 2-NSA tracer and "die-away" study clearly demonstrated the following facts:

(a) the 2-NSA served as an inert tracer which was not measurably adsorbed by, deposited within, or degraded by the industrial cooling water system under study;
(b) total removal of recirculating water from system was 40% higher than indicated from measurement of a blowdown flowmeter. The difference was traced to previously unaccounted losses of cooling water being used within the plant;
(c) the low concentration of treatment components was a result of low treatment feed rate due to previously unknown losses from cooling water system, not failure of treatment program;
(d) total volume of system (1.6M gal), total removal of recirculating water (370 gpm), and holding time index (50 hrs) were accurately quantified by 2-NSA and consistent with lithium results.

Use of treatment formulation which also contained 2-NSA fluorescent tracer (Test B) further verified that the formulation was being fed at only about 70% of desired level. Analysis of the $Zn^{+2}$ and phosphorus levels had incorrectly suggested the treatment concentration was even lower than 70% of desired value. Inclusion of 2-NSA in the treatment formulation clearly demonstrated the following:

(a) total removal of recirculating water from system was much higher than indicated by flowmeter on recirculating water blowdown pump;
(b) $Zn^{+2}$ and phosphorus analyses were not being properly conducted, resulting in erroneously low results;
(c) the low levels of treatment components resulted from a low treatment feed rate, not failure of the formulation to function effectively.

Accordingly, the feed rate of the treatment program was increased to compensate for the additional losses of recirculating water from the system.

There are numerous fluorescent tracers which are capable of equivalent performance as substitutes for 2-NSA or BAY8G, the concentration of which may be quantitatively measured at trace levels ranging from parts per trillion (ppt) to parts per million (ppm). Those fluorescent tracers may be soluble in water, organic solvents, inorganic solvents or mixtures of solvents chosen from one or more of the classes of liquids described. Those tracers may also be chosen from classes of materials which are excited by absorption of light and produce fluorescent light emission, where the excitation and emission light occurs at any point within the far ultraviolet to near infrared spectral regions (wavelengths from 200–800 nm). Combinations of one or more fluorescent tracers may also be used in combination with other fluorescent materials as long as the absorption of excitation light and emission of fluorescent light from the other components does not interfere with detection of light emission from the fluorescent tracers (refer to FIG. 5). Fluorescent tracers may also be used with other chemical agents, insert carriers, and in conjunction with nonfluorescing tracers as previously described.

Therefore, any material which is capable of fluorescing while dissolved or present in the performing liquid of a system or a liquid employed during analytical measurement of fluorescent emission may serve as a fluorescent tracer as long as it is inert to the system equipment and chemistry.

The use of fluorometry to quantitatively measure fluorescent tracers in liquid systems has special advantages compared to other trace analysis techniques as follows:

(a) very good selectivity as only a very small percentage of organic compounds fluoresce to a significant extent;
(b) a sufficient number of compounds are fluorescent so that, for any particular system, a tracer can be chosen for optimal performance (e.g. spectral properties, solubility, chemical inertness, low toxicity, etc.);
(c) tracers can be used in a broad range of organic and inorganic liquid systems ranging from polar solvents (such as water and alcohols) to nonpolar hydrocarbon solvents;
(d) very good selectivity is obtained since two spectral parameters can be varied and optimized (wavelength of light used to excite the tracer and the wavelength of fluorescence emission observed) as indicated in FIG. 5;
(e) proper choice of excitation light wavelength and fluorescent emission wavelengths provides ability to individually quantify one or more tracers, even in the presence of other fluorescent materials (FIG. 5);
(f) exceptional sensitivity with detection limits down to parts per trillion without requiring highly sophisticated equipment;
(g) proper choice of tracers provides very good resistance to changes in fluorescence emission due to system operating conditions (e.g. pH, temperature, dissolved salts, particulate matter, etc.)

In FIG. 1, the solid line represents observed values; the dashed line represents the ideal condition. The vertical axis is % relative emission (% em) under excitation. The tracer is symbol T. At all times concentrations (ppm T) are given in milligrams per liter, taken as ppm (parts per million) although the fluorescent tracers identified herein are sensitive to ppb (parts per billion).

In FIG. 2 most of the alphabet symbols have previously been defined. CA symbolizes treating component or components (e.g. phosphorus compounds, zinc compounds, etc), pH represents the reservoir of acid used for pH control and G represents equipment which measure pH′ and conductivity. Other instrumentation obviously may be present.

Figure 3:
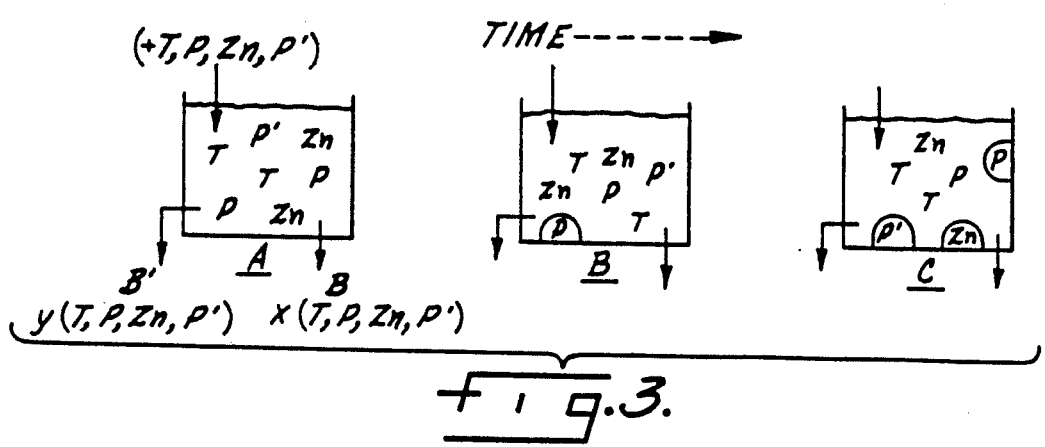

In FIG. 3 the treating components (CA) are P (phosphorus containing compound; e.g. organo-phosphorus compounds as scale and corrosion inhibitors); Zn (zinc cation) and P′ which designates a polymeric scale inhibitor, also one of the treating components. The "capped" symbols represent deposits; x and y are fractional amounts. B' represents the collective unaccounted losses of liquid from the system ($B_P + B_L + B_D$, etc.).

In FIG. 4, P has the same meaning as in FIG. 3, T has the same meaning as in FIG. 1 and ppm=concentration of formulation in system as calculated from tracer and total phosphorus content analyses.

In FIG. 5, the dashed curves are emission spectra, the solid curves are absorbance spectra. The left vertical axis is relative emission (% em) and the right vertical axis represents absorbance, contrasting two fluorescent tracers A and B; BK is background interference. FIG. 5 shows that for selected values for wavelengths of excitation light [$\lambda ex$ and $\lambda ex'$ in nanometers (nm); horizontal axis] the emission % at selected values for wavelengths of emission light ($\lambda em$ and $\lambda em'$) for the two tracers in the presence of each other is recognizably different and each is recognizably different from an (otherwise) interfering fluorescent compound (background) which might be present.

The data under this heading were based on grab samples, establishing the efficacy and reliability of using an inert tracer to audit system performance, disclosed and claimed in aforesaid Patent No. ---, giving rise to the continuous monitor and feedback control next to be explained.

Detailed Description: Continuous Monitoring of the Tracer

One form of instrumentation for continuous monitoring of the tracer and control over addition of the treating agent under the present invention contains four major components:

1. a sensor or detector including a flow cell for determining from an on-stream characteristic of the tracer how much product (treating agent) is present in the cooling water system based on analysis of a tracer added to the treatment, including a transducer which generates an electrical signal corresponding to that analysis;
2. feedback controller (monitor) that allows a power outlet, connected to the treating agent feed pump, to be activated and deactivated, depending on a comparison of the on-stream analysis of the concentration of treating agent in the cooling tower, represented by the voltage signal from the transducer, to a voltage standard representing par performance of treating agent;
3. an output recording device or other register that generates a record of the concentration of treating agent as a function of time; and
4. valves and all associated electrical circuitry to direct system water and calibrating solutions into the flow cell.

Figure 7:
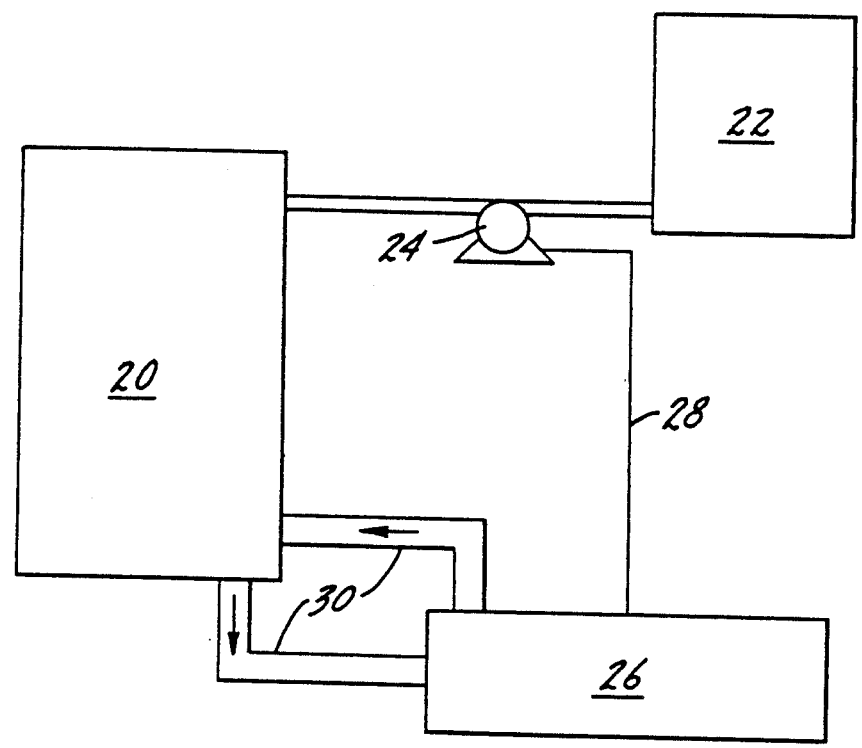
FIG. 7 is a diagram of a recirculating water tower cooling system with the present instrumentation interposed.

One system is shown in FIG. 7, more simplified compared to FIG. 2. The sources of makeup and blowdown water are not shown. Either source may be as large or larger than three or four hundred gallons per minute, and an error (from unknown sources) may be as much as or larger than one hundred gallons per minute. The enormity of these values, even limited to an hourly basis, can be readily recognized. The "product reservoir" 22 contains the proportioned treating agent and tracer, fed (pumped) into the circulating body of water used for cooling. The instrumentation for continuous measurement, monitoring and feedback control for the pump 24 is designated by reference character 26. A control line 28 will receive a signal when the instrumentation 26 detects a nonstandard performance. This signal may be used for any one of several equivalent pump functions for altering the pump output, that is, altering the dosage of treating agent and proportioned tracer. It may be used to alter the speed of a variable rate pump or to alter the displacement of a pump 24 in the form of a variable displacement pump. As another choice, the pumping system may include two pumps; one operating constantly (uncontrolled) to feed the treating agent and tracer at say 80% of the required amount. The other pump is a trim pump which makes up the difference (20%) and is the one which is controlled via control line 28.

When the system is in dynamic stability (on-stream) a sample of the body of water used for cooling is taken from the basin of the tower (or any other convenient location for that matter). The sample flows through a sampling line 30 (conduit) into a flow cell of the analyzer 26 where the prevailing on-stream concentration of tracer is compared to a standard representing standard or par performance of consumption of the treating agent. The concentration of treating agent is indicated by quantitation of the tracer concentration, which of course is equated to the treating agent concentration. In effect the treating agent concentration is measured on a real-time basis by analysis of the tracer.

The sampling line returns the sample to the basin. If the comparison shows nonstandard performance, a signal is generated in line 28 and the rate of dosage of treating agent (accompanied by the proportioned amount of tracer) is altered until par performance is attained. Nonstandard performance may be due to large, unknown additions of makeup water, diluting the treating agent so that the dosage is not enough to inhibit scaling and/or corrosion. Nonstandard performance may be due to large, unknown blowdown losses, by which the dosage of treating agent is drastically lowered.

The standard for measuring performance is based on past knowledge of the factors of the system, including impurity concentrations, area of tubing to be protected against corrosion or scaling, volume of water and rate of water flow. Using such factors, it is possible to calculate the dosage of treating agent. If an operating factor (parameter) is in error, especially the concentration of impurities to be inhibited by the treating agent, then nonstandard performance may be due to a miscalculated dosage, and not due to unexpected changes in water volume or water rates. In any event, the present instrumentation allows the treating agent dosage to be accurately trimmed to a prevailing cooling tower water system either by correcting the dosage when all operating parameters are accurately known, or by trouble shooting the system to identify unknown errors in the operating parameters.

The flow diagram for the instrumentation is shown in FIG. 8; the wiring diagram in FIG. 9. Under normal operation, water from the cooling tower basin 31 flows through a pressure regulator 32, through a solenoid valve 34-4 (normally open) and past a check valve 36 to the sample line leading to the analyzer 26. The return is through solenoid valve 34-2 (normally open), another check valve 38, and back into the cooling tower basin 31. The pressure regulator 32 insures that the pressure to the analyzer is always less than its maximum rated value. All water connections incorporate check valves to prevent back-flow of water into calibration solutions.

The analyzer is a Turner Designs Model Fluorometer 10 (Mountain View, Calif.) having a flow pressure rating of 25 psi. This fluorometer has the advantage of a two cm diameter, two inch long flow cell, which eliminates clogging of the sample stream, and also results in a large fluorescence intensity, fluorescence being proportional to cell pathlength. In general, any fluorometer, with a large pathlength, and excitation and detection in the ultraviolet. (UV) light region could be employed. However, a fluorometer, while preferred, is only one example of an analyzer for tracers, as will be mentioned in more detail below.

When calibration is desired, a bypass switch SW-1, FIG. 9, is actuated to open solenoid valve 34-1 (normally closed), while closing solenoid valve 34-4, thus diverting the water from the cooling tower basin around the fluorometer 26 via bypass line 44 and now-open solenoid valve 34-1. Solenoid valve 34-2 closes and 34-3 opens at the same time.

In preparation for calibration, the fluorometer cell is then rinsed by opening a rinse line via switch SW-2, opening normally closed solenoid valve 34-7 (normally closed). The rinse line is connected to a sample of a local makeup or fresh water which may feed line 46 by gravity fall.

After rinsing for approximately two minutes, the rinsing switch is opened, allowing valve 34-7 to close Valves 34-1, 34-2, 34-3 and 34-4 remain in the "bypass open" state. Calibration may now be undertaken.

A 0% calibration switch SW-3 is actuated which opens solenoid valve 34-5 (normally closed); solenoid valve 34-2 remains closed, and solenoid valve 34-3 remains open. The 0% calibration solution flows through the cell by gravity flow. The operator will then adjust a knob on the fluorometer indicator dial (see FIG. 10) until a reading of zero is obtained. The 0% calibration switch is then turned off. Valve 34-5 closes. The flow cell is rinsed again, letting the cell rinse for approximately two minutes. The full scale calibration of the instrument is performed by actuating on the 100% switch SW-4. This opens solenoid valve 34-6 (normally closed). The operator will then adjust a second knob on the fluorometer read-out dial until a full scale reading is obtained. To complete calibration the operator will turn off the 100% switch, again rinsing the flow cell for two minutes, and then turning the bypass switch SW-1 off. The instrumentation is now ready for continuous onstream monitoring of the treating agent concentration taken as the equivalent of the tracer concentration. Switch SW-5 is closed to bring in the pump 24 and switch SW-6 is closed to bring in the recorder (potentiometer) by which a continuous print-out of the treating agent concentration on a real-time basis is obtained Switch SW-7 is used to power the analyzer. It may be mentioned here that when the indicator dial is set for 0% and 100% indications, the recorder is also adjusted as well as the monitor, as will be explained.

A summary of the positions of the solenoids during each operation is given in Table II.

TABLE II

| Switch Turned ON | Solenoid # | Position (Open or Closed) | Energized, Not Energized |
|---|---|---|---|
| Fluorometer | 1 | Closed | No |
| | 2 | Open | No |
| | 3 | Closed | No |
| | 4 | Open | No |
| | 5 | Closed | No |
| | 6 | Closed | No |
| | 7 | Closed | No |

TABLE II-continued

| Switch Turned ON | Solenoid # | Position (Open or Closed) | Energized, Not Energized |
|---|---|---|---|
| Fluorometer Bypass | 1 | Open | Yes |
| | 2 | Open | No |
| | 3 | Closed | No |
| | 4 | Closed | Yes |
| | 5 | Closed | No |
| | 6 | Closed | No |
| | 7 | Closed | No |
| Rinse | 1 | Closed | No |
| | 2 | Closed | Yes |
| | 3 | Open | Yes |
| | 4 | Open | No |
| | 5 | Closed | No |
| | 6 | Closed | No |
| | 7 | Open | Yes |
| 0% Calibration | 1 | Closed | No |
| | 2 | Closed | Yes |
| | 3 | Open | Yes |
| | 4 | Open | No |
| | 5 | Open | Yes |
| | 6 | Closed | No |
| | 7 | Closed | No |
| 100% Calibration | 1 | Closed | No |
| | 2 | Closed | Yes |
| | 3 | Open | Yes |
| | 4 | Open | No |
| | 5 | Closed | No |
| | 6 | Open | Yes |
| | 7 | Closed | No |

The fluorometer 26 delivers an output of 0-5 volts (DC) corresponding to the amount of treating agent present in the system. This involves a transducer as will be explained. The amount of treating agent fed is controlled by a feedback signal emitted by a monitor MN which follows the output voltage of the analyzer, actuating "alarm" relays when the voltage signal from the fluorometer exceeds a HI setpoint, or falls below a LO setpoint. Standard performance lies between LO and HI.

The monitor is, for example, a Mighty Module model MM1020 DC Input Dual Limit Alarm (Wilkerson Instrument Co., Lakeland, Fla.). Because the relays on this monitor module do not necessarily provide enough current to power a chemical feed pump, a latching relay LR, FIG. 9, is included in the circuit. When the level of treating agent falls below the LO setpoint, the LO relay is energized, and this in turn energizes the latching relay, whereupon power is applied to the electrical outlet to which the chemical feed pump is plugged. The electrical outlet remains energized until the product level exceeds the HI setpoint in which event the HI relay on the monitor MN is energized, thus causing the latching relay to be reset as shown in FIG. 9 which disrupts power to the feed pump 24. One coil (not shown) communicated to the 0-5V. D.C. transducer controls all the relay contacts. Any other feedback controller (either analog, such as this one, or digital) may be used.

As noted, a recorder is preferably included so that a hard copy of the product concentration as a function of time can be obtained The recorder is preferably a Chessell Model 300 (0-5 V DC input, Chessell Corporation, Newton, Pa.) because its input impedance matches that of the fluorometer (3900 ohms). The input to the recorder is the 0-5 volt DC signal provided by the fluorometer.

Figure 10:
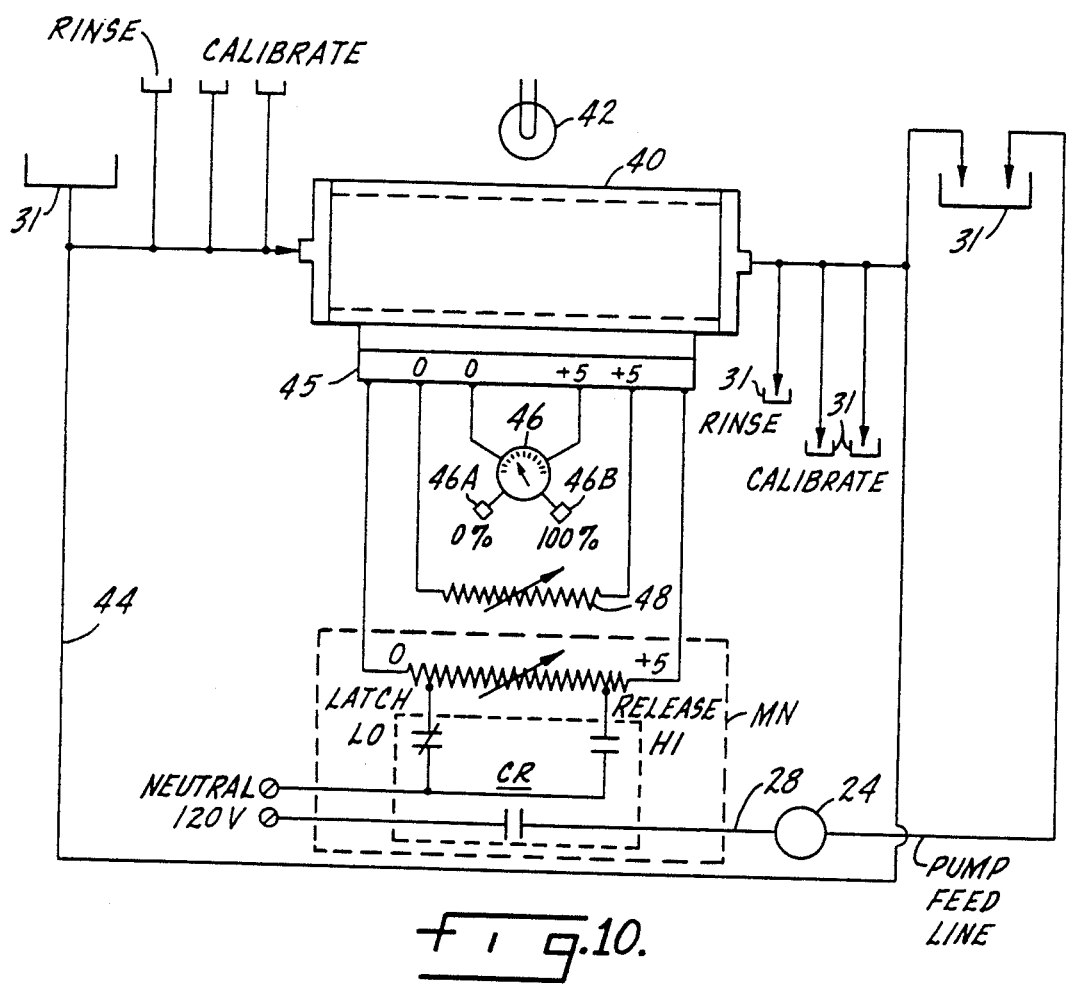
FIG. 10 is a schematic view of the instrumentation set-up of the present invention based on FIG. 8.

A summary of the instrumentation for continuous monitoring is presented in FIG. 10, schematically on an exaggerated scale. The flow cell is identified by reference character 40. It is a quartz cylinder having the dimensions noted above. The flow cell is transparent to ultraviolet emitted by a light source 42 directed against one side of the flow cell. At a 90° angle from the light source is a transducer 45 which transforms the emissivity of the fluorescent tracer into a 0-5 volt DC voltage, emissivity varying with concentration. Ultraviolet light excites the sample at a wave length of 290 nanometers and its emission is read at 330 nanometers when using the preferred fluorometer identified above.

A dial indicator 46 responds to the output voltage of the transducer 45 (0-5 volts DC) enabling the concentration of treating agent (tracer equivalent) to be observed. It is this dial which has the two knobs (46A,46B) respectively set manually for 0% calibration (no treating agent, no tracer) and 100% calibration (full treatment), mentioned above.

The recorder, for a hard printout of treating agent concentration, is identified by reference character 48, responding on an analog (continuous line) basis to the voltage output (0-5 volts, DC) of the transducer element included in the analyzer.

Finally, the monitor having the HI, LO latching relay contacts is in communication with the output voltage of the transducer which in effect evaluates the concentration of treating agent. If the evaluation does not compare favorably to the standard, the monitor transmits a control signal to the control line 28 by which pump 24 is controlled. A typical field condition may call for 200 ppm treating agent. During 0% calibration knob 46A is used to set the dial pointer (46) to zero and knob 46B (100%) is used to set the dial pointer to read the equivalent of 200 ppm when calibrating with the standard solution of treating agent and tracer.

There is invariably some background fluorescence in the cooling water. The tracer dosage should be powerful enough to overcome this interference, and in this connection the typical background interference is less than 10% for the fluorescent tracers identified above, which means the background is below an interference level according to classical analytical chemistry definitions.

It is not practical, or even necessary, to operate the system precisely at the optimum or standard tracer value, which, in this example, is 200 ppm. Thus, the setpoints in the monitor (LO, HI) may be chosen as 190/210, and these values represent the standard for comparison, that is, the voltage analog of the measured on-stream tracer emissivity is compared to the set points of the monitor. The corresponding LO, HI voltage range in the monitor MN may be 2.4/2.6, which is to say that when the monitor detects a LO value of 2.4 volts a control signal is emitted to increase the pump rate which continues until the HI value of 2.6 volts is detected. The analyzer response may drift after prolonged use, requiring recalibration from time to time, easily effected by the unique circuitry shown in FIGS. 8 and 9, involving on-stream switching to bypass, switching to rinse, switching to 0% calibration, re-rinse, switching to 100% calibration, re-rinse, and then switching back once again to on-stream monitoring of the treating agent performance, deemed par or standard in the range of 190/210 ppm. In this connection, as noted above, it is the treating agent concentration, under constant flow, which is continuously monitored on a real-time basis under the present invention, and not some unreliable fragmented operating parameter such as water gains or water losses, or grab sample averaging. Thus, calibration is accomplished without removing any of the instrumentation and without interrupting movement of the sample stream which is merely diverted to the bypass line 44.

Temperature Compensation

If the instrument is calibrated using room temperature tap water (equivalent to system makeup water, say 58° F.) but the system is running at a considerably higher temperature (say 82° F.) calibration will not present the correct ppm standard for comparison. Specifically, if the instrument is calibrated at 58° F. to read 200 ppm "product" (treating agent) but the cooling water system is on-stream at 82° F., the analyzer would indicate a product level of 167 ppm, instead of 200 ppm, an unacceptable error beyond experimental error.

This chance of error can be compensated in several ways. One way is to use a calibration plot, correcting for the difference. Better still, since the calibration solutions may be in containers, feeding the calibration lines (FIG. 8) by gravity, the solutions can be warmed to the on-stream temperature.

The equation for temperature compensation (change in fluorescent intensity=CFI) for the tracers used is given by:

$$CFI = -0.32\,(T^\circ C.) - 0.8$$

for the temperature range 60° to 115°. This compensation can be handled yet another way, namely, to add a microprocessor chip and thermocouple to the analyzer circuitry by which the on-stream fluorescent intensity undergoes compensation in accordance with the above equation.

Indeed, the instrumentation in its entirety may be controlled by microprocessing so that the operator need not perform manually the numerous valving and switching sequences for calibration explained above in connection with FIGS. 8 and 9. One microprocessor unit for accomplishing this is an OPTO 22 (Huntington Beach, Calif.). Using such a processor it is only necessary for the operator to use a main off-on switch, an "operate" button, a "calibrate" button, a "0%" calibrate button and a "100%" calibrate button. Temperature compensation, discussed above, is embodied in the OPTOMUX processor chip.

A colorimeter or spectrometer (responsive to Rhodamine WT) may be substituted for the fluorometer and its associated units (transducer, recorder, monitor) since all three portions of the analyzer can convert the spectral characteristics of the tracer to an electrical signal, where the signal output is a voltage value for example related to the concentration of tracer present. The fluorometer measures intensity of light emission under illumination, the colorimeter measures absorbance, as would a spectrophotometer. All are deemed photometers herein, each capable of exciting a tracer, flowing through a flow cell, by electromagnetic (light) radiation and transforming the light emission or light absorption into an electrical analog output (e.g. voltage) on a continuous basis.

Field Experience: FIGS. 8-12
First Form of Continuous Fluorescence Monitor/Feedback Control Unit After laboratory testing using pilot cooling towers, the instrumentation was evaluated at a chemical plant. The evaluation, which was a great success, resulted in:
(a) a dramatic improvement in control of the chemical (treating agent) program, translated into improved program results;
(b) a significant net decrease in chemical program costs due to the elimination of overfeeding.

The chemical plant began using a nonmetal treating agent program in 1986 in an effort to eliminate the use of two potentially hazardous chemicals, sulfuric acid and gaseous chlorine. Sulfuric acid was eliminated by choosing a polymeric treating agent and organic phosphonate which did not require pH control to be effective. Gaseous chlorine was replaced by a solid bromine based biocide program effective at alkaline pH ranges.

While the bromine based biocide replacement was successful from the very beginning, the organic phosphate polymeric inhibitor was not well received by the tower operators. The test for this product at the opening stage of operation involved a digestion-by-boiling procedure, and several color development steps that required precise and time consuming waits after each reagent was added. Additionally, due to the difficulty of running the procedure successfully, test results were frequently suspect. Occasionally adjustments to feed rates indicated by test results were not made on a timely basis because those running the test assumed the test was in error, not the actual chemical feed rate to the tower.

Because of the difficulties associated with quantifying the concentration of organophosphonate based inhibitor, it was decided to have the daily water tests run by a quality assurance lab rather than by operations personnel. This step improved the repeatability of the test results but added a definite "lag" to the time period between an out-of-range test condition being discovered and when it was acted upon.

When plant personnel suggested the need for improvement in the inhibitor test procedure, our instrumentation was proposed, enabling laboratory personnel in the plant to determine product level by measuring the tracer level in the cooling water, rather than a treatment component. The tracer analysis was accomplished by simply placing a sample of the cooling system water into the analysis cell and instantly reading it (a 30 second grab sample procedure). This was a significant improvement from the previous 25-30 minute organophosphonate analysis procedure that included boiling and addition of multiple reagents in the color development step.

Figure 11:
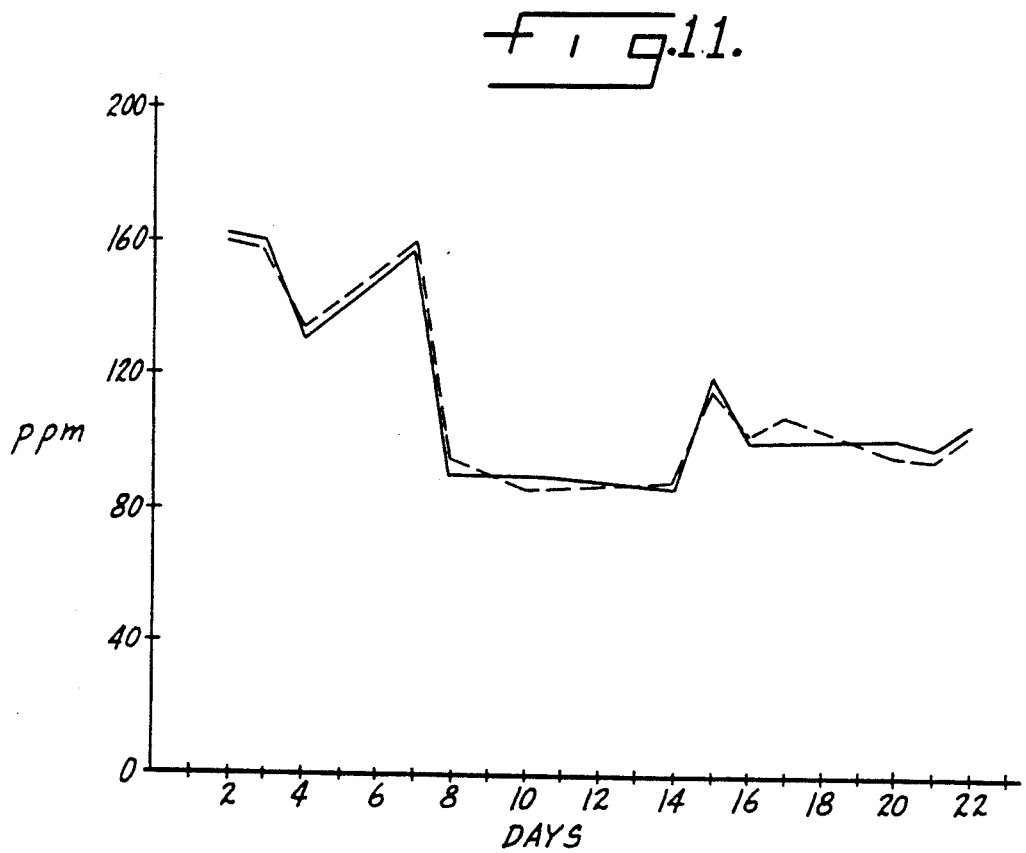
FIG. 11 is a replicate graph comparing tracer (solid line) and quantitative analyses (dashed line) values.

For a reasonable trial period (22 days) both the grab sample tracer test and the grab sample regular product test (total phosphorus content) were run by two analysts on replicate samples As there was good correlation (see FIG. 11) between the two tests, management for the industrial plant decided to switch to the fluorescent tracer method as the normal plant control test. In FIG. 11, the solid line is the tracer grab sample readout; the dashed line is precision quantitative (phosphonate) analysis (grab sample) by the quality assurance lab at the plant.

Although testing was greatly simplified and the accuracy greatly improved, precise control of the treatment program continued to be a problem due to fluctuations in the cooling system operating parameters. Data collected earlier showed readings as high as 63 ppm and as low as 8 ppm, although the desired specification limits were 35-45 ppm. Fully 58% of all the readings taken were out-of-range on either the high or the low side due to variability in the operation of the cooling system.

When these data were analyzed the need for continuous monitoring and feedback control of the treatment concentration (via the tracer method) was clearly evident. Statistical presentation of the data showed a Process Capability Ratio (PCR) of only 0.129 (PCR should be >1) with a standard deviation of ±13 ppm (or ±32% relative error). A normal distribution curve of the data (histogram) showed an exceptionally wide curve, with a definite skew towards out-of-range low readings; FIG. 18.

Because the primary concern was equipment integrity, out-of-range low readings for treatment concentration were considered totally unacceptable. Failure to provide adequate levels of treatment chemical was known to result in fouling and scaling of heat transfer equipment which would be anathema to both production rates and production efficiency.

Given the looseness of the existing control process when maintained by analysis of grab samples from cooling water system, it was decided to evaluate raising the specification limits (aiming point or target) to whatever was required to insure that a minimum level (35 ppm) of chemical was always present. Statistical analysis revealed that given the existing wide variability in the control of the plant's cooling water system, chemical treatment would have to be targeted at 64 ppm to maintain at least 35 ppm 99.73% of the time. This represents a considerable waste of treating agent at considerable cost.

The necessity for implementing the "aim high to hit low" program was avoided by adopting the present continuous monitoring/feedback control instrumentation to automatically sense the tracer level in the flow cell and to adjust product feed in response to the demand signal from the monitor.

Figure 12:
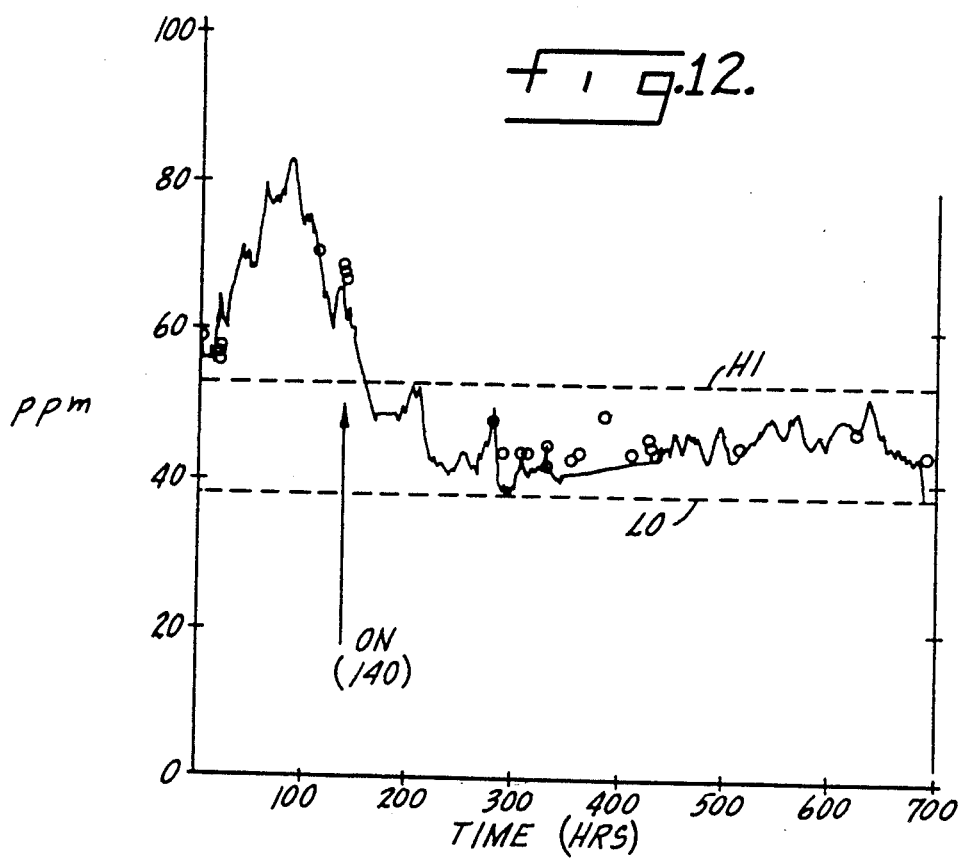
FIG. 12 is a replicate field trial graph showing typical continuous monitor performance of the present instrument (solid line) compared to actual (dots) grab samples.

Initially, the instrumentation was used to continuously monitor chemical treatment level only (hours 0-140, FIG. 12), during which control was provided, as previously, by manually adjusting the chemical feed pumps in response to test result reports from quality assurance. After 140 hours it was established the instrumentation could correctly and reliably read the quantity of treatment present in the tower, corroborated by numerous lab-tested grab samples (circles, FIG. 12) compared to concentrations measured continuously by our instrumentation; correlation was excellent. FIG. 12 is typical of the tight control over product feed possible under the present invention.

The instrumentation of the present invention was then placed on-stream to automatically regulate chemical feed on a continuous real-time basis, accomplished by two chemical metering pumps: a base feed pump operated continuously at approximately 50% of the calculated chemical treatment requirement, and a second trim pump receiving the control signal from line 28, FIG. 7, set to turn "on" (lower set limit, LSL) at 38 ppm, and to turn "off" (upper set limit, USL) at 48 ppm. The results were completely successful, FIG. 12. For over 560 hours (twenty-three days), the analyzer, FIG. 9, reliably controlled product feed within a control range of 38-48 ppm. Standard deviation was reduced from almost ±12.9 ppm (FIG. 18) to a little over ±3.2 ppm. This reduction is shown in FIG. 19: 96 readings, mean value 44. 458 ppm, max. 52, min 38; LSL of 35, USL of 45; sigma 3.225.

In summary, control of the chemical inhibitor level was improved almost fourfold with significantly reduced requirements for manpower and cooling rate analyses. The equipment performed very well during the entire 30-day evaluation, requiring neither maintenance nor calibration. Post evaluation analysis of the data indicated that a 30% chemical treatment savings was possible as compared to using the previously described "aim high to hit low" approach which would have resulted in overfeeding the product to make sure that all treatment concentration readings would be above the lower specification limit of 35 ppm.

Figures 1, 14:
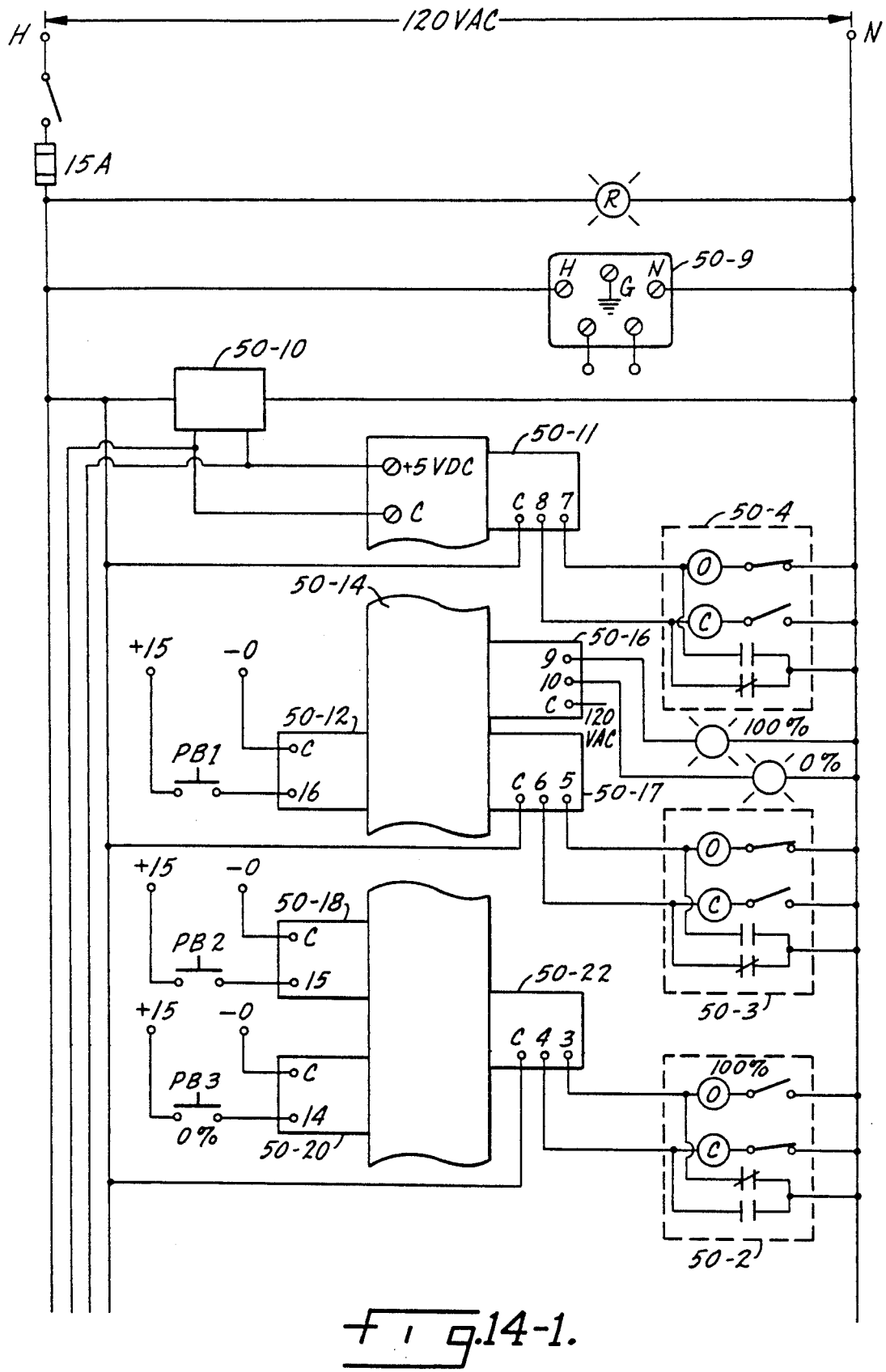
Figures 2, 14:
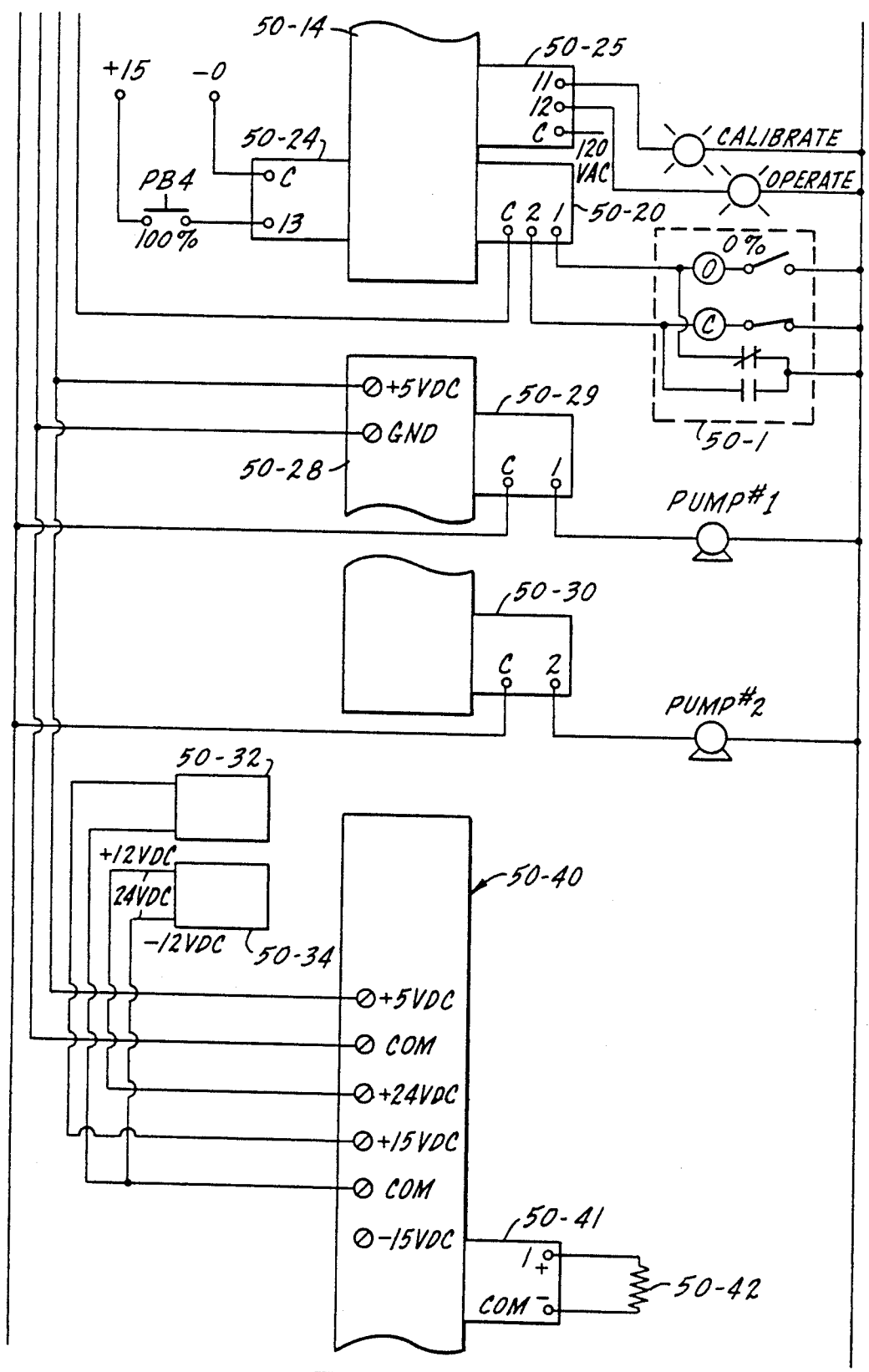
Figures 3, 14:
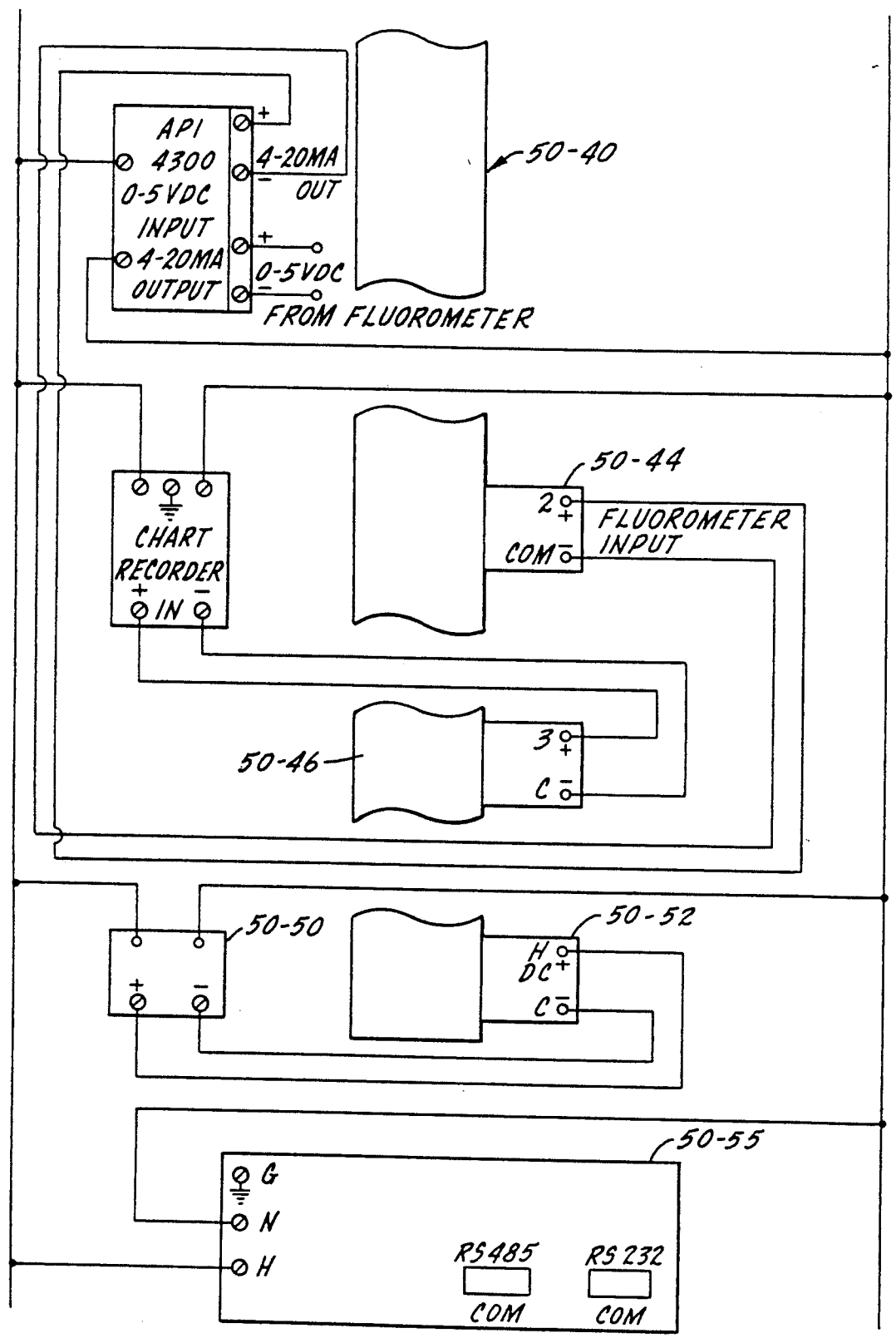

Second Form of Continuous Fluorscence Monitor Feedback Control Unit: FIGS. 13 and 14

The second instrument included a microprocessor to automatically control the calibration of the instrument, and to adjust the fluorescence output to compensate for changes in the cooling water temperature. This unit incorporates four motorized ball valves, instead of the solenoid and check valves used in the previous unit. The water flow diagram is given in FIG. 13. The fluorometer and related units are the same as used in the first instrument. Under normal operation, valves 50-3 and 50-4 (2-way ball valves), are closed Valve 50-1 is a 3-way T-diversion valve and directs the cooling water coming from the cooling tower basin through the fluorometer. Valve 50-2 is also a 3-way T-diversion valve and directs the water coming out of the fluorometer back to the cooling tower basin. The calibration sequence can be performed manually, by pressing a calibration button on the front panel of the instrument, or automatically, at a user specified interval. During a calibration sequence, valve 50-1 diverts the water coming from the cooling tower basin immediately back to the basin, thereby bypassing the fluorometer. Valve 50-2 diverts the water coming out of the fluorometer to the drain. Valves 50-3 and 50-4 are opened when 0% calibration and 100% calibration are performed, respectively.

The circuitry used in this instrument is shown in FIG. 14 and comprises four major parts: a microprocessor controller with associated memory, digital to analog converters, analog to digital converters, and signal conditioners. The microprocessor system used in the instrument was an OPTOMUX microprocessor made by Opto 22 (Huntington Beach, Calif.), comprising a digital and an analog brain board, both connected to an LC4 controller board. The analog board enables the transducer signals from the fluorometer and the temperature probe to be input into the microprocessor. The signal to the chart recorder also originates from this board. Finally, the monitor setpoint at which power is applied to the chemical feed pump is input into the microprocessor through this board via an Altec 4-20mA setpoint control.

The digital brain board allows the microprocessor to determine when any buttons on the front panel (for manual calibration) are activated. In addition, the digital board provides the outputs necessary to activate the ball valves, and the chemical feed pumps. A signal conditioner (API 4300 0-5V DC input, 4-20 mA output) is used to convert the voltage signal from the fluorometer into a 4-20 mA signal. The 4-20 mA signal is more common in industrial process control instrumentation, since it is more resistant to electrical noise. Appropriate power supplies (+5 volt, +15 volt), used to power the microprocessor and appropriate boards are also used.

The instrument, FIG. 13, operates in much the same fashion as the first instrument, FIG. 10. The electrical outlet that supplies power to the chemical feed pumps is energized when the product, determined by the voltage signal from the fluorometer after temperature compensation, drops below the monitor setpoint specified by the Altec setpoint control. The electrical outlet (control line 28) is turned off when the product exceeds the setpoint plus 5%, a value specified by the program stored in the memory of the LC4 controller.

The signal from the fluorometer is adjusted by the microprocessor to account for changes in the temperature of the cooling water. The fluorescence intensity of any molecule usually decreases with increasing temperature. This is because other pathways by which the excited molecule can relax, besides fluorescence, become more probable at higher temperatures. The temperature of the water flowing through the fluorometer is determined by a temperature probe placed in the flow stream, immediately before the fluorometer. A temperature probe (RTD) was used instead of a thermocouple to obtain the desired accuracy and precision in the temperature determination. The difference between the temperature that the instrument was calibrated at, and the current temperature of the cooling water is determined, and the appropriate correction factor is applied to the fluorometer signal to obtain the temperature compensated product concentration. This is also the signal that is sent to the recorder.

In FIG. 14 the following units are involved in the wiring diagram:
Ball valves: 50-1, 50-2, 50-3 and 50-4
0-5VDC to 4-20 Signal Conditioner: 50-9
5 VDC power supply: 50-10
OPTO 0 AC5Q output: 50-11 (one of four outputs per quad pak)
Switch PBI: operate
OPTO IDC 58Q, 4-16 VDC INPUT: 50-12 Note: C=Common
OPTO PB16 HQ B1 ADDRESS 253:50-14
OPTO OAC 5Q: 50-16
OPTO OAC 5Q OUTPUT: 50-17
Switch PB2: Calibrate
OPTO CIDC 5AQ, 4-16 VDC INPUT: 50-18
OPTO ICD 58Q, 4-16 VDC INPUT: 50-20
Switch PB3: 0% calibrate
OPTO OAC 5Q OUTPUT: 50-22
Switch PB4: 100% calibrate
OPTO IDC 58Q, 4-16 VDC INPUT: 50-24
OPTO OAC 5Q: 50-25
OPTO OAC 5Q OUTPUT: 50-26
OPTO PB16HQ+B1 ADDRESS 252: 50-28
OPTO OAC 5Q OUTPUT: 50-29
OPTO OAC 5Q OUTPUT: 50-30
+15 VDC Power Supply: 50-32
+12 VDC Power Supply: 50-34
OPTO PB4AH+B2 OPTO RACKS CONNECTED VIA COMMUNICATIONS TERMINAL: 50-40
OPTO ADIOT RTD INPUT: 50-41
TEMPERATURE- PROBE: 50-42
OPTO AP3 4-20, 4-20 ma INPUT 50-44
OPTO DA4 0-5 VDC OUTPUT: 50-46

ALTEC 4-20 SETPOINT CONTROL: 50-50
OPTO 4-20 ma DC INPUT (AD3)
LC4 CONTROLLER: 50-55
PIN L -- Instrument ground
PIN M -- 0-5VDC OUTPUT The LC4 controller 50-55 is connected to the analog brain (B2) and digital brain board (B1) via the communication terminals at 50-40.

Monitoring By Colorimeter and Ion Selective Electrode

Colorimetry or spectrophotometry may be employed as noted above. The schematic arrangement is shown in FIG. 15, using a Brinkman PC-801 probe colorimeter (570 nm filter). The sample solution is admitted to a flowcell 62 in which a fiber optic (dual) probe 64 is immersed. One fiber optic cable shines incident light through the process liquid onto a mirror 66 inside the cell and reflected light is transmitted back through the process liquid into a fiber optic cable and then to the colorimetric analyzer unit by the other cable as shown by arrows. The colorimeter 60 has a transducer which develops an electrical analog signal of the reflected light characteristic of the tracer concentration. The voltage emitted by the transducer activates a dial indicator 67 and a continuous line recorder printout unit 68. A set point voltage monitor (not shown, but as in the foregoing embodiments) will constantly sense (monitor) the voltage analog generated by the colorimeter and if nonstandard performance is established a signal is transmitted to line 28 to alter accordingly the feed rate of the pump supplying the chemical treatment.

An ion selective electrode may be employed to determine the concentration of an inert tracer ion ($K^+$ is a good example) in terms of the relationship between the electrical signal developed by the electrode and the concentration of tracer. By calibration (potential or current vs concentration) the ionic concentration at the sample electrode can be indexed to a reference (standard) electrode which is insensitive to the tracer ion. To provide continuous monitoring of the tracer, the electrodes may be dipped directly into a flowing stream of the cooling water, collectively constituting a flow cell, or the cooling water could be passed through an external flow cell into which the ion-selective and reference electrodes have been inserted.

An example of a flow cell incorporating an ion selective electrode system is shown in FIG. 16, comprising a PVC (polyvinyl chloride) sensor base or module 70 containing the reference and sample electrodes (cells) respectively denoted 72 and 74, each including a silver/silver chloride electrode wire, and a grounding wire 76. These electrodes constitute an electrochemical cell across which a potential develops proportional to the logarithm of the activity of the selected ion which may be $K^+$.

An 8 pin DIP socket 78 will be wired to a standard dual FET ("field effect transistor") op amp device. The sample of recirculating cooling water is conducted across the electrodes by a flexible tube 80; the tracer ions penetrate only the sample (ion selective) electrode cell 74.

The FET op amp device (a dual MOSFET op amp) is thus connected to the flow cell shown in FIG. 16 to perform the impedance transformation, whereby the potential difference between the reference and sample electrodes may be obtained, using an amplifier, FIG. 17.

Here, FIG. 17, the transducer is in effect the ionophore membrane 74M of the sample electrode allowing the selected ion activity (concentration) to be transformed to a weak voltage which when amplified can be monitored between set points as in the foregoing embodiments.

The present method of continuous monitoring and resultant feedback to control the feed rate of the treating agent allows for additional diagnostic supervision in addition to the feedback control just mentioned. By following the recorder or hard print-out records, aberrations, anomalies and system faults are readily perceived and can be corrected as the case may be. Examination of the performance record on the first day (after allowing for system equilibration) may reveal consumption of ten pounds of treating agent, for example, whereas the second day record may show twenty pounds (to continue the example) even though the product concentration was being held constant based on monitoring the tracer. A divergence in product usage of this scale would demand investigation, and the investigation may reveal development of a serious leak in the system, not a mere aberration or anomaly, requiring a correction to cure the water loss. The diagnosis of performance based on tracer readings and product usage may be otherwise, e.g. an increase in the blowdown rate, and the correction may require a reduction in the blowdown rate.

The continuous monitor record may reveal high or low concentrations of the treating agent, but of short duration which can be placed in the anomaly class to be ignored. On the other hand, high or low treatment corrections of appreciable duration or continuity cannot be ignored, requiring investigation. Such investigation may take into account the same time of day for several days past, for which another supervisor may very well have logged an explanation.

If the record establishes need for more, or less, treating agent than was thought, the rate of change can be estimated or even calculated by a differential equation since the print-out establishes both time and concentration changes. Thus, the operator can estimate or calculate the increase or decrease in product feed rate, the more readily to restore the system to balance, and thereafter for the steady state rate of feed.

Use of a single inert tracer may be employed to monitor a brace of treating agents (one for scaling, one for corrosion) when the two treating agents are fed proportionally, say a high rate pump feeding one product at twice the rate of a second product dosed by a pump whose feed rate is directly tied (slaved) to the first. Since the tracer will be proportioned to one of the two treating agents, it is, by definition under this invention, proportioned to the other.

The invention represents a considerable advance over the current practice of taking grab samples, running them to the analysis room, waiting for the analytical report and then manually adjusting a knob on a pump controller. Grab samples, at best, must be averaged to be interpreted and when interpreted represent past performance some time ago not present performance on an instantaneous real-time basis which in part characterizes the present invention. This is most evident from FIGS. 11, 12, 18 and 19. In this connection it may be mentioned that in FIGS. 18 and 19 the abscissa is the frequency of finding the grab sample value represented by the ordinate (ppm) and from this alone it can be realized how many grab samples must be generated to obtain a meaningful average curve represented by the superimposed normal distribution curves in these two figures. In comparison, note again the narrow horizontal band in FIG. 12 evidencing compliance with the upper and lower set voltage limits representing standard performance.

Hence, while we have illustrated and described preferred embodiments of the invention it is to be understood these are capable of variation and modification within the purview of the appended claims.

We claim:

1. In a cooling water system where an on-stream body of water is employed in a heat exchange role, there being a source of makeup water addition to the system as well as a source of blowdown water removal from the system, wherein impurities in the body of water, likely to cause corrosion or scaling of equipment confining the body of water, are inhibited by introducing a treating agent which undergoes depletion in its inhibiting role within the system, the treating agent being introduced proportionally with a tracer which is inert to the system including equipment and chemistry:
   instrumentation including an analyzer having a flow cell for receiving a sample of the circulating on-stream body of water and for sensing a characteristic of the tracer indicative of its concentration, said analyzer having a transducer for converting said characteristic to a voltage analog thereof;
   a monitor for receiving said voltage analog and for continuously comparing it to a voltage standard representing a standard tracer concentration constituting par performance in consumption of the treating agent, said monitor generating an output signal when said comparison establishes nonstandard performance;
   and a pump unit for introducing the proportioned treating agent and tracer at a predetermined dosage; said output signal controlling said pump unit to alter the dosage.

2. A system according to claim 1 wherein the tracer characteristic is generated by illuminating the sample with electromagnetic radiation.

3. A system according to claim 2 wherein the tracer is fluorescent and the sample is passed through a flow cell in the form of a ceramic cylinder, the cylinder being transparent to light and illuminated so emissivity of the tracer may be measured 4. A system according to claim 1 wherein the standard concentration of treating agent is within a predetermined range of ppm, wherein the monitor has adjustable low and high set points which limit and define that range in terms of concentration of proportioned tracer, wherein the monitor generates an output signal to increase the pump unit output when the low setpoint is reached and generates a signal to discontinue the increased pump output when the high setpoint is reached 5. A system according to claim 4 wherein the pump unit comprises a main pump for running constantly to supply a major portion of the treating agent and tracer dosage, and a trim pump controlled by said signal to supply the remaining dosage.

6. A system according to claim 1 wherein the flow cell is in a sample line through which the on-stream sample of cooling water passes;
   a bypass line and related valving to deny the on-stream water sample to the cell and divert the denied sample back to the circulating body of water to enable rinsing and calibration to be accomplished;
   a line for passing rinse water and subsequently zero percent calibration water through the cell while calibrating the instrumentation for zero percent treating agent;
   and a line for passing through the flow cell a dosage of treating agent and tracer quantified thereto representing one hundred percent standard dosage for on-stream treatment while calibrating the instrumentation thereto.

7. System according to claim 1 including a sample line for withdrawing an on-stream source of the circulating body of water as a sample, for passing the sample through the flow cell to be analyzed therein, and for returning the analyzed sample to the stream.

8. In a cooling water system where a body of water is employed in a heat exchange role, there being a source of makeup water addition to the system as one system parameter as well as a source of blowdown water removal from the system as another system parameter, wherein impurities in the body of water likely to cause corrosion or scaling of equipment confining the body of water are inhibited by introducing a treating agent as a third parameter of the system, which undergoes depletion in its inhibiting role within the system, the system including a pump unit for feeding to the body of water, at a predetermined dosage, the treating agent proportionally with a tracer which is inert to the system including equipment and chemistry, a method of continuously monitoring performance of the treating agent comprising the steps of:
   passing continuously a sample of the on-stream body of water through a flow cell and therein continuously sensing a characteristic of the tracer indicative of its concentration;
   converting said characteristic to a voltage analog thereof;
   constantly comparing said voltage analog to a voltage standard representing a standard tracer concentration constituting par performance in consumption of the treating agent;
   and altering one of said parameters, to restore the system to par performance, when said comparison indicates nonstandard performance for the treating agent.

9. Method according to claim 8 wherein the tracer characteristic is radiant energy generated by illuminating the sample in a photometer.

10. A method according to claim 9 wherein the tracer is fluorescent and including the step of passing the sample through a quartz cylinder transparent to and illuminated by light.

11. A method according to claim 8 wherein an output signal is generated when said comparison establishes nonstandard performance for the treating agent and including the step of employing said signal to alter the output of the pumping unit until standard performance is attained.

12. A method according to claim 11 wherein the pump unit comprises a main pump to be run constantly to supply a major portion of the treating agent and tracer dosage, and a trim pump to supply the remaining dosage, and including the step of employing said signal to control the rate of the trim pump.

13. A method according to claim 8 including the additional step of selecting as the voltage standard that which lies between a low voltage value and a high voltage value respectively limiting a range of standard ppm treating agent, increasing the pump output when the voltage analog is at or below the low voltage value and decreasing the pump output when the voltage analog is at above the high voltage value.

14. In a heat exchange system where a body of water is employed in a heat exchange role, there being sources of makeup water additions to the system as a system parameter as well as sources of blowdown water removal from the system as another system parameter, wherein impurities in the body of water, likely to cause corrosion or scaling of equipment confining the body of water, are inhibited by introducing a treating agent, as a third system parameter, which undergoes depletion in its inhibiting role within the system, the treating agent being introduced by a pump unit proportionally with a tracer which is inert to the system including equipment and chemistry:

instrumentation for continuously monitoring performance of the treating agent including an analyzer for receiving a continuous sampling of the body of water and for continuously sensing a characteristic of the tracer indicative of its concentration, said analyzer having a transducer for continuously converting said characteristic to a voltage analog thereof;

a monitor for receiving said voltage analog and for comparing it to a voltage standard representing a standard tracer concentration constituting par performance in consumption of the treating agent;

and means responsive to said comparison for indicating nonpar performance of the treating agent whereby one of said parameters may be audited and corrected as responsible for nonpar performance.

15. System according to claim 14 wherein said responsive means generates an output signal used to alter the output of the pump unit to alter the rate at which the treating agent and tracer are introduced.

16. A system according to claim 15 wherein the tracer characteristic is radiant energy generated by illuminating the sample in a photometer.

17. A system according to claim 16 wherein the tracer is fluorescent and the sample is passed through a flow cell in the form of a quartz cylinder, the cylinder being illuminated to excite the fluorescent tracer the emissivity of which is measured and converted to a voltage analog.

18. A system according to claim 14 wherein the standard concentration is a predetermined operating range of ppm tracer, wherein the voltage standard is a range between predetermined low and high voltage values defining that range, wherein the monitor generates an output signal to increase the output of the pump unit when the low setpoint is reached and generates a signal to discontinue the increased output when the high setpoint is reached.

19. A system according to claim 18 wherein the pump unit comprises a main pump running constantly to supply a major portion of the treating agent and tracer dosage, and a trim pump controlled by said signal to supply the remaining dosage.

20. A system according to claim 14 wherein the analyzer includes a flow cell in a sample line through which the on-stream sample of cooling water passes;

a bypass line and related valving to deny the on-stream water sample to the cell and divert the denied sample back to the circulating body of water to enable rinsing and calibration to be accomplished;

a line for passing rinse water and subsequently zero percent calibration water through the cell while calibrating the instrumentation for zero percent treating agent;

and a line for passing through the flow cell a dosage of treating agent and tracer quantified thereto representing one hundred percent standard dosage for on-stream treatment while calibrating the instrumentation thereto.

* * * * *